(12) United States Patent
Kundu et al.

(10) Patent No.: US 10,233,273 B2
(45) Date of Patent: Mar. 19, 2019

(54) PARAFFIN SUPPRESSANT COMPOSITIONS, AND METHODS OF MAKING AND USING

(71) Applicant: Ecolab USA Inc., St. Paul, MN (US)

(72) Inventors: Kousik Kundu, Houston, TX (US); Jeremy Moloney, Katy, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/617,627

(22) Filed: Jun. 8, 2017

(65) Prior Publication Data

US 2017/0355798 A1 Dec. 14, 2017

Related U.S. Application Data

(60) Provisional application No. 62/348,384, filed on Jun. 10, 2016.

(51) Int. Cl.
| | | |
|---|---|---|
| C08F 210/00 | (2006.01) | |
| C08F 222/06 | (2006.01) | |
| C09K 11/65 | (2006.01) | |
| G01N 21/64 | (2006.01) | |
| G01N 33/28 | (2006.01) | |
| C09K 8/524 | (2006.01) | |

(52) U.S. Cl.
CPC .......... *C08F 222/06* (2013.01); *C08F 210/00* (2013.01); *C09K 8/524* (2013.01); *C09K 11/65* (2013.01); *G01N 21/643* (2013.01); *G01N 33/2835* (2013.01); *C09K 2208/10* (2013.01); *G01N 2021/6419* (2013.01); *G01N 2021/6421* (2013.01); *G01N 2021/6439* (2013.01)

(58) Field of Classification Search
USPC .................. 524/95; 508/305; 507/200, 219
See application file for complete search history.

(56) References Cited

U.S. PATENT DOCUMENTS

| | | | |
|---|---|---|---|
| 3,436,373 A | 4/1969 | Cox et al. | |
| 4,783,314 A | 11/1988 | Hoots et al. | |
| 5,702,684 A | 12/1997 | McCoy et al. | |
| 6,566,139 B2 | 5/2003 | Davis et al. | |
| 8,956,541 B2 | 2/2015 | Elliott | |
| 8,956,875 B2 | 2/2015 | Kahaian et al. | |
| 2011/0254432 A1 | 10/2011 | Zeininger | |
| 2014/0121350 A1 | 5/2014 | You et al. | |
| 2015/0041406 A1 | 2/2015 | Xiao et al. | |
| 2016/0108327 A1* | 4/2016 | Pulikkathara | B01D 21/01 166/304 |
| 2016/0231247 A1 | 8/2016 | Abla et al. | |

FOREIGN PATENT DOCUMENTS

| | | |
|---|---|---|
| WO | 2014089214 A2 | 6/2014 |
| WO | 2015174996 A1 | 11/2015 |
| WO | 2016025051 A2 | 2/2016 |
| WO | 2016053711 A1 | 4/2016 |

OTHER PUBLICATIONS

Pan et al., "Hydrothermal Route for Cutting Graphene Sheets into Blue-Luminescent Graphene Quantum Dots", Advanced Materials, 2010, vol. 22, No. 6, pp. 734-738.
Bacon et al., "Graphene Quantum Dots", Particle & Particle Systems Characterization, vol. 31 No. 4, 2014, pp. 415-428.
Karpicz et al., "Laser Fluorosensor for Oil Spot Detection", Lithuanian Journal of Physics, vol. 45, No. 3, 2005, pp. 213-218.
Xu et al., "How comb-type poly(maleic acid alkylamide-co-α-olefin) assemble in waxy oils and improve flowing ability", Asia-Pacific Journal of Chemical Engineering, vol. 4; pp. 551-556, 2009.
Andreev et al., "Laboratory assessment of corrosion inhibitors effectiveness at oilfield pipelines of West Siberian region. III. Bubble test", Int. J. Corros. Scale Inhib., vol. 2, No. 1, pp. 17-29, 2013.
Kelland, Malcolm A. "History of the Development of Low Dosage Hydrate Inhibitors", An American Chemical Society Journal, Energy & Fuels, vol. 20, No. 3, May/Jun. 2006, pp. 825-847.
Jin et al., "Tuning the Photoluminescence of Graphene Quantum Dots through the Charge Transfer Effect of Functional Groups", ACS Nano , vol. 7, No. 2, pp. 1239-1245, 2013.
Wu, et al., "Fabrication of highly fluorescent graphene quantum dots using L-glutamic acid for in vitro/in vivo imaging ans sensing", Journal of Chemistry C, 2013, pp. 4676-4684.
Hluchan, et al., "Amino acids as corrosion inhibitors in hydrochloric acid solutions", Materials and Corrosion, 39(11), Nov. 1, 1988, pp. 512-517.
Muhammad, et al., "The Use of Glutamic Acid as Corrosion Inhibitor for Aluminium in Hcl Solution", IOSR Journal of Applied Chemistry, 7(2), Mar.-Apr. 2014, pp. 50-62.

(Continued)

*Primary Examiner* — Terressa Boykin
(74) *Attorney, Agent, or Firm* — Kagan Binder, PLLC

(57) ABSTRACT

Disclosed herein are graphene quantum dot tagged paraffin suppressants such as graphene tagged paraffin inhibitors and paraffin dispersants and methods of making and using thereof. The graphene quantum dots are covalently bound to residues of paraffin inhibitors or dispersed with paraffin dispersants to form tagged paraffin suppressants active in inhibiting paraffin crystallization or dispersing crystalized paraffin wax in crude oils and compositions comprising crude oils. The dots can be tailored to fluoresce at wavelengths with minimized correspondence to the natural fluorescence of crude oils, enabling the measurement of the concentration of the paraffin suppressants in crude oils or compositions comprising crude oils. The tagged suppressants are used to trace the dispersion and disposition of the paraffin suppressants in oils and compositions comprising them, for example within crude-oil recovery, production, processing, or conveyance and transportation, by in situ sampling the oil or composition and measuring the fluorescence of the sampled material.

15 Claims, 6 Drawing Sheets

(56) References Cited

OTHER PUBLICATIONS

Zheng, et al., "Glowing Graphene Quantum Dots and Carbon Dots: Properties, Syntheses, and Biological Applications", retrieved from http://onlinelibrary.wiley.com/doi/10.1002/smll.201402648/epdf, Apr. 8, 2015, pp. 1620-1636.
International Search Report for International Application No. PCT/US2017/036540, dated Oct. 18, 2017 (6 pages).
Written Opinion for International Application No. PCT/US2017/036540, dated Oct. 18, 2017 (7 pages).
Bacon, et al., "Graphene Quantum Dots", Particle & Particle Systems Characterization, 31(4), Nov. 27, 2013, pp. 415-428.
Zhu, et al.,"Surface Chemistry Routes to Modulate the Photoluminescence of Graphene Quantum Dots: From Fluorescence Mechanism to Up-Conversion Bioimaging Applications", Advanced Functional Materials, 22(22), Nov. 21, 2012, pp. 4732-4740.
Sun, et al., "Highly Photoluminescent Amino-Functionalized Graphene Quantum Dots Used for Sensing Copper Ions", Chemistry—A European Journal, 19(40), Aug. 12, 2013, pp. 13362-13368.
International Search Report for International Application No. PCT/US2017/036545, dated Aug. 21, 2017 (6 pages).
Written Opinion for International Application No. PCT/US2017/036545, dated Aug. 21, 2017 (8 pages).
Layek, et al., "A review on synthesis and properties of polymer functionalized graphene", Polymer, 54(19), Aug. 1, 2013, pp. 5087-5103.
Song, et al., "Study on the relationship between the structure and activities of alkyl methacrylate-maleic anhydride polymers as cold flow improvers in diesel fuels", Fuel Processing Technology, 86(6), Mar. 25, 2005, pp. 641-650.
International Search Report for International Application No. PCT/US2017/036550, dated Aug. 3, 2017 (6 pages).
Written Opinion for International Application No. PCT/US2017/036550, dated Aug. 3, 2017 (7 pages).

\* cited by examiner

PARAFFIN SUPPRESSANT COMPOSITIONS, AND METHODS OF MAKING AND USING

FIELD OF THE INVENTION

The present invention generally relates to tagged paraffin suppressant compositions, methods of making using them.

BACKGROUND

Crude oil products are globally obtained from subterranean reservoirs using techniques such as drilling and hydraulic fracturing. Transportation of crude oil products from the subterranean reservoir, required to refine or process the crude oil, is accomplished by moving the crude oil through pipes and into storage/transportation means such as rail cars, tanks, and the like. During the moving and/or storage, the crude is often subjected to ambient temperatures between −40° C. and 60° C.

Crude oil products include linear and branched alkanes having the general formula $C_nH_{2n+2}$ wherein n is typically about 1-50, although minor amounts of longer hydrocarbon chains do occur. The higher molecular weight alkanes can be problematic in that their melting points tend to be greater than ambient temperatures in some cases. For example, nonadecane has a melting point of 33° C.; higher alkanes can have melting points in excess of 60° C. for example.

The high melting alkane fractions lead to phase separation of paraffinic residue that solidifies and deposits on the sides and bottoms of pipes, storage vessels, and transportation vessels (rail cars, ocean tankers, etc.). The solid, phase separated paraffinic residue, also known as "paraffin wax", not only reduces the effective volume of the structure within which it is contained but also represents a loss of a valuable component from the body of the crude oil. Excessive paraffin wax buildup reduces the efficiency of transporting crude oil and leads to increased costs related to added downtime for cleaning of the pipes and/or vessels as well as disposal of residues removed from the vessel which increase environmental burden. While the pipelines and vessels can be cleaned to remove the paraffinic residue, the process generates hazardous waste, takes the vessel out of service during the cleaning period, and is expensive.

The phase separation of paraffin wax can be reduced by additives, called "paraffin inhibitors" (PI) which interfere with the crystallization process of wax and/or suspend wax crystals in the oil. Typical paraffin inhibitor polymers include, e.g. ethylene polymers and copolymers thereof with vinyl acetate, acrylonitrile, or α-olefins such as octene, butene, propylene, and the like; comb polymers with alkyl side chains such as methacrylate ester copolymers, maleic-olefinic ester copolymers, and maleic-olefinic amide copolymers; and branched copolymers having alkyl side chains such as alkylphenol formaldehyde copolymers and polyethyleneimines.

The phase separation of paraffin wax can also be reduced by additives, called "paraffin dispersants" (PD), which disperse wax and/or paraffin crystals which form in the oil. Many paraffin dispersants are oligomeric or small surfactant molecules. Examples of paraffin dispersants include nonylphenol formaldehyde resins, and dodecyl benzene sulfonic acid-.

The addition of a paraffin suppressant (a paraffin inhibitor or a paraffin dispersant or both) or a "paraffin suppressant concentrate" (PSC) to the crude oil is effective in dispersing paraffinic residue, thereby reducing the formation of residues in the pipelines and vessels to the benefit of the oil and gas industry. Paraffin suppressant effectively reduces the formation of paraffinic residues during storage and transportation of the crude oil products, mitigating economic loss and decreasing environmental impact. A majority of operators in the oil and gas industry employ paraffin suppressant as their primary mode of paraffinic residue control in production pipelines. Non-aqueous formulations including such paraffin suppressant concentrate (PSC) are transported to and stored at the field locations where crude oil is recovered so that it can be applied as needed to pipes, vessels, and the like. Providing PSC in a fluid format—i.e. in solution or dispersion—is highly advantageous for applying PI in the field because pumping equipment suitable to meter the desired amount of PI into a pipe or vessel is readily available.

A suite of laboratory tests under simulated field conditions are conventionally conducted before field deployment to identify the preferred paraffin suppressant and the optimal paraffin suppressant dosage to reach the operator's various performance requirements. Such laboratory tests include cold-finger experiments and cold filter plugging tests. When used in the field, paraffin suppressant is added to crude oil products in production equipment such as pipes and tanks at a rate initially to target a laboratory-determined concentration of paraffin suppressant to prevent and/or disperse paraffinic residue. Because of differences between the laboratory and field environments, it is advantageous to optimize the paraffin suppressant addition rate in the field, typically based on paraffin monitoring which is assumed to be representative of the system. The paraffin monitoring is further complemented with paraffin suppressant residual analysis, that is, measurement of residual paraffin inhibitor and/or paraffin dispersant concentration at the end of a pipe. However, in systems lacking means of paraffin monitoring, operators often rely solely on residual paraffin suppressant monitoring to ensure that the concentration of the paraffin suppressant concentration is within a targeted range. For example, samples can be sent to a laboratory for liquid chromatography/mass spectroscopy analysis. However, at present there is no method for paraffin suppressant analysis of oilfield samples in the field. A field method for residual paraffin suppressant analysis would be advantageous, because results could be obtained more quickly, and real-time adjustments to addition rate and/or other dosage means to control paraffin suppressant concentration in the oil could be made, maintaining an effective and economic dosage of paraffin suppressant to prevent paraffin deposition without use of excessive quantities of paraffin suppressant.

Therefore, there is a need for paraffin suppressants and paraffin suppressant compositions that can be applied to crude oil or compositions containing crude oil in oil-recovery, oil transportation, and oil processing facilities, and wherein the paraffin suppressant concentration can be determined in situ at various selected locations, including those in the field distant from laboratory facilities, and can be monitored by sampling at different locations of the facilities.

SUMMARY OF THE INVENTION

Disclosed herein are polymers comprising the residue of polymeric paraffin inhibitors covalently bound to a graphene quantum dot fluorescent tags. In embodiments, the graphene quantum dot has a particle size of 2 nm to 20 nm. In embodiments, the paraffin inhibitor is effective at inhibiting the phase separation of paraffin waxes in crude oil.

In embodiments, the paraffin inhibitor comprises the monomer residues of one or more α-olefins and one or more imide residues, wherein the graphene quantum dot is covalently bonded to the nitrogen of the imide residue. In embodiments, the one or more imide residues comprises maleimide residue, nadimide residue, citraconimide residue, or other substituted maleimide residue.

In embodiments, the paraffin inhibitor comprises an ethylene-vinyl acetate copolymer and has a graphene quantum dot covalently bonded thereto.

Also disclosed herein are paraffin inhibitor premixes, the premixes comprising one or more monomers, wherein at least one of the one or more monomers has one or more graphene quantum dots bonded thereto. In embodiments, a paraffin inhibitor premix comprises an amine-functionalized graphene quantum dot, a substituted phenol, and formaldehyde. In embodiments, a paraffin inhibitor premix comprises an acrylate, methacrylate, substituted acrylate monomer, an ethylene vinyl acetate polymer, one or more olefins, vinyl acetate, a free radical initiator, or a mixture thereof; and an acrylamido-functionalized graphene quantum dot having the formula (VI)

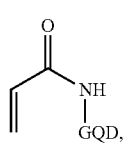

(VI)

wherein GQD represents a graphene quantum dot having a particle size of about 2 nm to 20 nm. Also disclosed are polymers made by polymerizing any of the premixes disclosed herein, wherein the monomers of the premix react with one another and one or more functionalized quantum dots to form a polymeric graphene tagged paraffin inhibitor. Also disclosed are methods of making polymeric graphene tagged paraffin inhibitors comprising subjecting any of the paraffin inhibitor premixes disclosed herein to conditions suitable for polymerization.

Also disclosed herein are graphene tagged paraffin dispersant compositions comprising graphene quantum dots and paraffin dispersants dispersed in a hydrophobic liquid. In embodiments, the hydrophobic liquid is a hydrocarbon solvent. In embodiments, the graphene quantum dots have a particle size of about 2 nm to 20 nm.

Also disclosed herein are crude oil compositions comprising one or more crude oils, any of the graphene tagged paraffin inhibitors and/or any of the paraffin dispersants and/or paraffin dispersant compositions disclosed herein. In embodiments, the graphene tagged paraffin inhibitors are present at about 5 ppm to 5000 ppm by weight in the crude oil composition. In embodiments, the concentration of the graphene quantum dot in the crude oil composition is from 0.1 ppb to 1000 ppb.

Also disclosed are methods of making graphene tagged paraffin inhibitors comprising grafting one or more of acrylate ester, acrylic acid, methacrylic acid, and maleic anhydride to an ethylene-vinyl acetate copolymer to form a grafted polymer, and attaching an amine-functionalized graphene quantum dot to the grafted polymer to form a graphene-tagged paraffin inhibitor.

Also disclosed are methods of tracing paraffin suppressant in crude oil comprising adding a graphene-tagged paraffin suppressant composition comprising any of the paraffin inhibitors and/or paraffin suppressant compositions disclosed herein to a crude oil composition comprising a crude oil to form a graphene tagged crude oil composition, irradiating the graphene tagged crude oil composition with a source of light having a selected first range of wavelengths; and measuring a fluorescent emission of the graphene quantum dot at a selected second range of wavelengths, wherein the measuring is carried out substantially contemporaneously with the irradiating. In embodiments, the method further comprises measuring a fluorescent emission of the graphene quantum dot at a selected range of wavelengths, wherein the measuring is carried out substantially contemporaneously with the irradiating. In embodiments, the second range of wavelengths is between about 600 nm and 700 nm. In embodiments, the second range of wavelengths is substantially a single second wavelength. In embodiments, the single second wavelength is about 600 nm. In embodiments, the first range of wavelengths is substantially a single first wavelength. In embodiments, the single first wavelength is about 500 nm.

Also disclosed are methods of making a graphene tagged crude oil composition, the method comprising adding one or more organic solvents to any of the graphene tagged paraffin inhibitors disclosed herein and adding the concentrate to crude oil.

Also disclosed are uses of a graphene tagged paraffin suppressants or graphene tagged paraffin suppressant compositions for determining the concentration of a paraffin inhibitor in a crude oil composition.

DETAILED DESCRIPTION

Figure 1:
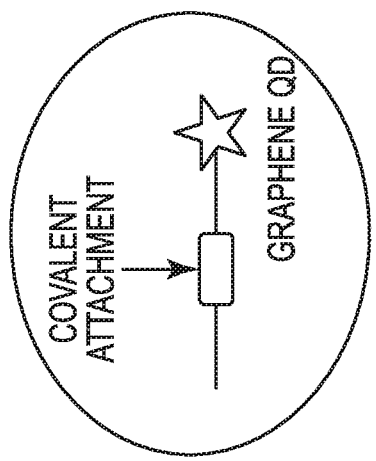
FIG. 1 illustrates a general synthetic scheme for a graphene quantum dot tagged paraffin inhibitor of the invention.
Figure 1:
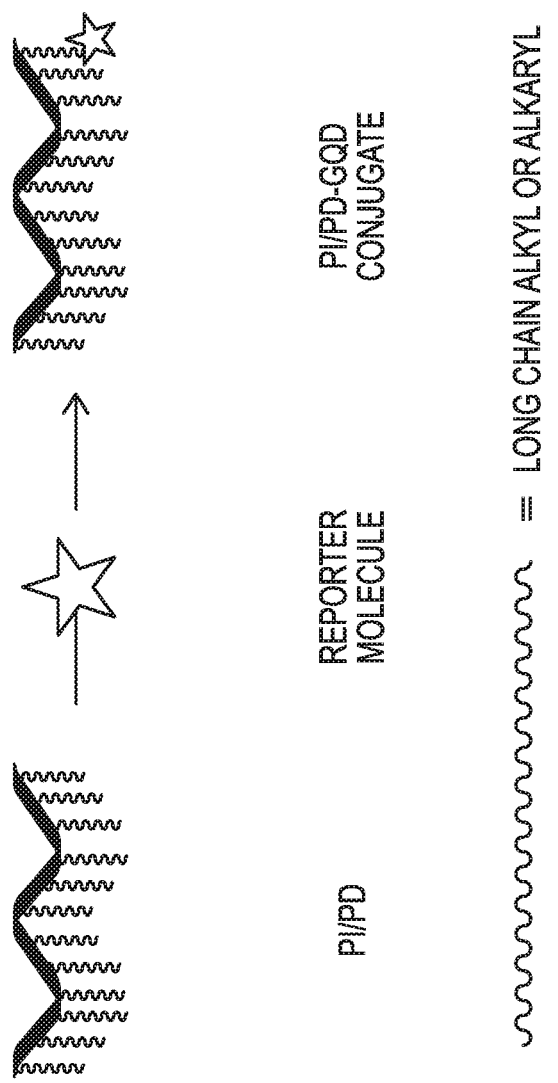

Although the present disclosure provides references to preferred embodiments, persons skilled in the art will recognize that changes may be made in form and detail without departing from the spirit and scope of the invention. Various embodiments will be described in detail with reference to the drawings. Reference to various embodiments does not limit the scope of the claims attached hereto. Additionally, any examples set forth in this specification are not intended to be limiting and merely set forth some of the many possible embodiments for the appended claims.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)", "include(s)", "having", "has", "can", "contain(s)", and variants thereof, as used herein, are intended to be open-ended transitional phrases, terms, or words that do not preclude the possibility of additional acts or structures. The singular forms "a", "and", and "the" include plural references unless the context clearly dictates otherwise. The present disclosure also contemplates other embodiments "comprising", "consisting of" and "consisting essentially of", the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, rate, concentration, partition coefficient, solubility, temperature, and the like; intended values include yield, weight, concentration, and the like. The effect on methods that are modified by "substantially" include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" the claims appended hereto include equivalents to these types and amounts of materials.

As used herein, the term "entraining in" means dispersing in, dissolving in, suspending in, mixing in, or combinations thereof.

As used herein, "copolymer" means a polymer comprising more than one type of monomer residue. This includes terpolymers, tetrapolymers, and polymers comprising more than four types of monomer residue. Similarly, as used herein, the term "comonomer" are not intended to be limited to one of two monomers but include one of more than one type of monomer, where more than one type of monomer for example includes two monomers, three monomers, four monomers, or more than four monomers.

As used herein, the term "crude oil" means the unrefined hydrocarbon product of a subterranean reservoir, wherein the product is a liquid or a solid at 20° C. at a pressure of about 1 atmosphere, the product including at least linear and branched alkanes having the general formula $C_nH_{2n+2}$ wherein n is typically about 1-50, and can be greater than 50.

As used herein, "mixing" one or more materials means any form of bringing into contact the one or more materials without limitation as to the order of mixing of the materials or whether the materials continue to exist in their original form before the addition of all of the materials is complete.

As used herein, the terms "spectrometry" and "spectroscopy" means the process of analyzing the interaction between a sample of matter and electromagnetic radiation to determine one or more physical properties of the sample of matter. Forms of electromagnetic radiation used include but are not limited to one or more of microwave, terawave, infrared, near infrared, visible, ultraviolet, x-ray, radiation. The analysis includes measurements of one or more of the radiation's absorption, emission, fluorescence, colorimetric, color changes, reflection, scattering, impedance, refraction, and resonance by the sample of matter.

As used herein, the term "paraffin suppressant" (PS) means paraffin inhibitor or paraffin dispersant, or a mixture thereof. A paraffin suppressant is an additive for crude oil which is effective for suppressing the phase separation of paraffin wax from crude oil. "Suppressing the phase separation of" here means retarding, delaying, minimizing, reducing, inhibiting, or preventing the phase separation of; or dispersing or dissolving after phase separation.

As used herein, the term "paraffin suppressant concentrate" (PSC) means a composition comprising one or more paraffin suppressants dissolved, dispersed, or otherwise entrained in a medium such as an organic solvent or mixture of organic solvents at a first concentration, the composition for use as an additive miscible with crude oil to produce a paraffin suppressed crude oil composition, wherein the crude oil composition comprises the paraffin suppressant dissolved, dispersed, or otherwise entrained in the paraffin suppressed composition at a second concentration which is lower than the first concentration and wherein at the second concentration the paraffin suppressant is effective for suppressing the phase separation of a paraffin wax in the crude oil composition.

As used herein, the term "paraffin inhibitor" (PI) means a polymeric and/or oligomeric chemical or chemical mixture, wherein the inhibitor retards, delays, minimizes, reduces, inhibits, or prevents the phase separation of paraffin wax from crude oil to which it is added.

As used herein, the term "paraffin dispersant" (PD) means a oligomer or short-chain material such as a surfactant, which disperses, dissolves, stabilizes, or otherwise entrains a paraffin wax in crude oil when added to the crude oil.

As used herein, the term "tagged paraffin inhibitor" (t-PI) means a paraffin inhibitor covalently bonded to one or more chemical moieties capable of fluorescence when subject to incident light.

As used herein, the term "functionalized graphene quantum dot" (GQD*) means a graphene quantum dot with one or more graphene functional groups covalently bonded thereto, wherein the one or more graphene functional groups are capable of condensation, addition, or other reaction with one or more paraffin inhibitor functional groups or in a paraffin inhibitor premix, thereby causing the graphene quantum dot to be covalently bonded to a PI residue yielding a graphene tagged paraffin inhibitor.

As used herein, "paraffin inhibitor functional group" means a chemical group on a paraffin inhibitor capable of reacting with one or more functional groups on a functionalized graphene quantum dot yielding a graphene tagged paraffin inhibitor.

As used herein, the term "paraffin inhibitor residue" means a paraffin inhibitor, wherein one or more functional groups on the paraffin inhibitor have been reacted with a functionalized graphene quantum dot.

As used herein, the term "paraffin inhibitor premix" (PI premix) means a mixture of chemical compounds comprising a functionalized graphene quantum dot and one or more monomers, wherein one or more components of the mixture are capable of reacting to form a polymeric or oligomeric graphene tagged paraffin inhibitor.

As used herein, the term "graphene tagged paraffin inhibitor" (Gt-PI) means a paraffin inhibitor residue covalently bonded to one or more graphene quantum dots (GQD).

As used herein, the term "graphene tagged paraffin dispersant" (Gt-PD) means one or more paraffin dispersants bound in inverse micelle or micelle form with one or more graphene quantum dots.

As used herein, the term "graphene tagged paraffin suppressant" (Gt-PS) means a graphene tagged paraffin inhibitor or a graphene tagged paraffin dispersant.

As used herein, the term "paraffin suppressant composition" means a composition comprising, consisting of, or consisting essentially of a paraffin suppressant.

As used herein, the term "graphene tagged paraffin suppressant composition" means a composition comprising, consisting of, or consisting essentially of a graphene tagged paraffin suppressant.

As used herein, the term "graphene tagged paraffin suppressant concentrate" (Gt-Conc) means a composition comprising at least one graphene tagged paraffin suppressant and a solvent/dispersant, wherein the at least one graphene tagged paraffin suppressant is dissolved, dispersed, and/or otherwise entrained in the solvent/dispersant. In embodiments, the concentrate further comprises one or more of additional solvents, one or more ester compounds and/or one or more other types of pour-point depressant, one or more surfactants, one or more additional paraffin suppressants, and/or mixtures thereof. The one or more additional paraffin suppressants comprise one or more paraffin suppressants without a tag, one or more paraffin suppressants with a tag, or mixtures thereof. In embodiments, the solvent/dispersant is a hydrocarbon solvent.

As used herein, the term "graphene tagged crude oil composition" (Gt-PS/CO) means a composition comprising at least one graphene tagged paraffin suppressant and crude oil. In embodiments, a graphene quantum dot tagged paraffin suppressant crude oil composition further comprises one or more of solvents, surfactants, other additives known in the art, or mixtures thereof.

As used herein, "crude oil composition" means any composition which comprises, consists of, or consists essentially of crude oil. Non-limiting examples of a composition comprising crude oil include crude oil, crude oil plus a paraffin suppressant concentrate, crude oil plus a paraffin suppressant, crude oil plus one or more organic solvents, and crude oil plus one or more additives.

As used herein, the term "crude oil containment" means any object which holds, is designed to hold, or is capable of holding crude oil. Non-limiting examples of crude oil containment include pipelines, storage tanks, sumps, reservoirs, tank cars, tank trucks, downhole tubing, and tubing annuli, as well as devices which hold or convey crude oil such as gauges, taps, meters, pumps, and valves.

As used herein, the term "crude oil conveyance" means any means and/or object which facilitates the movement of crude oil. Non-limiting examples of crude oil conveyance include pipelines, tank cars, tank trucks, downhole tubing, tubing annuli, as well as devices which facilitate the movement of crude oil such as taps, pumps, and valves.

As used herein, the term "ester compound" means a non-polymeric compound having at least one ester moiety, for example in some embodiments one ester moiety, in other embodiments two ester moieties, in still other embodiments three ester moieties, and in still other embodiments more than three ester moieties.

As used herein, the term "non-aqueous" means substantially excluding water.

As used herein, the term "liquid", "flows", or "flow" referring to a composition of the invention means that 10 mL of the composition vertically at rest on a substantially horizontal surface in a cylindrical container having dimensions of radius 1 inch and height 2 inches flows observably within about 10 seconds when tipped to a substantially horizontal position. In some embodiments, "liquid", "flows", or "flow" referring to a composition of the invention means a composition that has a Brookfield viscosity at 10 $s^{-1}$ of about 5 cP to 1000 cP.

Discussion

In complicated oil extraction, oil-processing, and oil-transportation operations and the facilities therefor, for example enhanced oil-recovery systems such as gas-lift applications, it is very difficult to monitor paraffin suppressant concentrations because of the complicated and various pathways by which paraffin suppressant is disposed throughout the systems. It would be advantageous to measure paraffin suppressant concentration at various positions, stages, and times in a crude oil production process and/or crude oil conveyance and transportation.

Furthermore, it would be extremely advantageous to trace paraffin suppressant concentration in the field, because it could enhance understanding of paraffin inhibition and/or dispersion and could lead to better design of next-generation paraffin inhibitors and paraffin dispersants.

Thus, improved residual analysis techniques for paraffin inhibitors and paraffin dispersants are needed. Specifically, there is a need in the industry to provide compositions and methods for rapid paraffin inhibitor and/or paraffin dispersant concentration measurement in crude oil production. There is a need for such compositions and methods to useful on-demand and in the field during subterranean hydrocarbon recovery processes. There is a need for such compositions and methods to provide rapid results that enable such measurements to be made in real time. There is a need for such compositions and methods to provide resolution of one or more distinct paraffin inhibitor and/or paraffin dispersant species from other paraffin suppressant species, from other additives present in the crude oil products, and from the hydrocarbon products of the crude oil.

Fluorescence "tagging", that is, covalently attaching a fluorescent molecule to a paraffin inhibitor or paraffin dispersant molecule, is a potential method for providing such a means of quantifying a single species of paraffin inhibitor or paraffin dispersant a crude oil composition. In such an embodiment, an operator in the field could simply excite a sample of crude oil product (crude oil or a composition containing crude oil) by irradiating it with a selected range of wavelengths of light, specifically within the excitation range known to cause fluorescence of the fluorescent tagged paraffin suppressant, and measure the resulting amount of fluorescence emission generated by the fluorescent tagged paraffin suppressant. However, major impediments exist in implementing such imaging technologies due to the presence of intrinsic background fluorescence emitted by the hydrocarbons which crude oil products comprise, such as the fluorescence from crude oil and/or the fluorescence from condensates. Further, fluorescent molecules selected have different photophysical properties that further can be significantly affected by covalently attaching the fluorescent molecule to a paraffin inhibitor or a paraffin dispersant. In some cases, fluorescence is reduced below a useful level or is even quenched by interaction with a particular paraffin suppressant.

If such issues were overcome, it would be advantageous to use such fluorescent molecules or structures to monitor paraffin suppressant concentration downhole in oil-recovery operations, as well as in post-recovery operations such as oil processing, refining, storage, and transportation. However, conditions of temperature, pressure, and chemical exposure can be extreme under such circumstances, especially downhole in oil-recovery operations. Therefore there is a need for fluorescent materials that can withstand such extreme conditions and maintain consistent fluorescent properties (such as absorbance, emittance, absorption and/or emission spectra) under such conditions.

The present Applicants have found that graphene quantum dots are useful as fluorescent tag tracers for paraffin inhibitors, paraffin dispersants, and other chemicals used in oil-recovery, oil-processing, and oil storage and transportation applications, where the graphene quantum dots unpredictably show many advantages over other tags and/or tracers and solve the aforementioned problems. Graphene quantum dots exhibit excellent stability to higher temperatures and against chemical reactivity and quenching. Additives such as paraffin suppressants, when in oil pipeline, production, or downhole subterranean locations can be subject to extreme conditions of temperature, pressure, pH, and corrosive and reactive chemicals: any tracer molecule and/or tag needs to be stable under such conditions, as noted above. Graphene quantum dots are advantageously used in such locations, environments, and/or conditions, and are more stable chemically than many other types of fluorescent molecule under the harsh conditions found in such environments. Graphene quantum dots may be covalently or otherwise chemically attached or associated with paraffin suppressants, and the graphene quantum dot tags can be tailored to minimize absorption spectra or emission spectra overlap with the absorption and/or emission spectra of crude oils and compositions containing the crude oils to which they are added.

In embodiments, a composition of the invention comprises, consists essentially of, or consists of a paraffin inhibitor compound (PI) covalently bonded to one or more graphene quantum dots (GQD) to form a graphene tagged paraffin inhibitor (Gt-PI). In other embodiments, the invention comprises, consists essentially of, or consists of a graphene quantum dot dispersed in one or more organic solvents by one or more paraffin dispersants to form a graphene tagged paraffin dispersant. In embodiments, the graphene quantum dot of the graphene tagged paraffin inhibitor and/or the graphene quantum dot of the graphene tagged paraffin dispersant produces fluorescence with emission wavelengths that are substantially non-overlapping with characteristic emission wavelengths of various hydrocarbon products in the crude oil, thereby making it possible to monitor and trace individual paraffin inhibitors and/or paraffin suppressants in the crude oil in real time in the field and/or at various points in the recovery, processing, and/or transport of crude oil and compositions containing crude oil. In such embodiments, the emission intensity at a specific fluorescence wavelength is proportional and/or related to the concentration of the graphene tagged dispersant or inhibitor, and is used to obtain the concentration thereof. In embodiments, the specific intensity is the emission at λmax (the wavelength at which maximum emission occurs). In other embodiments, there is an amount of overlap between the emission wavelengths of one or more hydrocarbons and the emissions wavelengths of the Gt-PI, because the fluorescence spectrum of hydrocarbons can be very broad and also because hydrocarbon composition varies depending on the source of the crude oil. Crude oil can exhibit fluorescence from polyaromatic and/or asphaltene molecules within the oil. In embodiments, an overlap between the emission spectrum of the crude oil and the emission spectrum of the graphene quantum dot. In embodiments where such an overlap in emissions spectra exists, a correction factor is introduced to address this effect, the known background emission spectrum of the crude oil can be subtracted from the measured omission spectrum to obtain the emission spectrum of the graphene quantum dot tag. The emission at λmax of the emission spectrum of the graphene quantum dot can thereby be obtained—the emission is proportional and/or related to the concentration of the graphene quantum dot tag and therefore the paraffin inhibitor. In embodiments, the emission spectrum of the crude oil overlaps the absorption fluorescence spectrum of the graphene quantum dot. If the emission spectrum of the crude oil overlaps with the excitation (absorption spectrum) of the graphene quantum dot, emission from the crude oil can excite extra fluorescence in the graphene quantum dot, i.e. fluorescence transfer from the fluorescing hydrocarbons to the graphene quantum dot. In embodiments wherein such fluorescence transfer exists, a correction factor is introduced to compensate for the change in apparent emission at given concentrations of the graphene quantum dot.

A quantum dot is a nanometer-scale particle wherein excitons are confined in all three spatial dimensions. GQD are graphene fragments that are small enough to cause exciton confinement and a quantum size effect. Typically, GQD have diameters of less than about 20 nm. Due to the fact that all graphene fragments exhibit quantum confinement effects, GQD have a non-zero bandgap and luminesce upon excitation. The bandgap is tunable by modifying the size and surface chemistry of the GQD. Overall, the spectroscopic properties of GQD vary depending on the method of preparation and/or functional groups bonded to the GQD at the edge(s) of the particles, and the size of the GQD.

The GQD useful in any embodiment or all embodiments herein without limitation include those having an average particle size of about 1 nm to 20 nm, or about 2 nm to 20 nm, or about 3 nm to 20 nm, or about 4 nm to 20 nm, or about 5 nm to 20 nm, or about 6 nm to 20 nm, or about 7 nm to 20 nm, or about 8 nm to 20 nm, or about 9 nm to 20 nm, or about 10 nm to 20 nm, or about 11 nm to 20 nm, or about 12 nm to 20 nm, or about 13 nm to 20 nm, or about 14 nm to 20 nm, or about 15 nm to 20 nm, or about 16 nm to 20 nm, or about 17 nm to 20 nm, or about 18 nm to 20 nm, or about 19 nm to 20 nm, or about 1 nm to 10 nm, or about 2 nm to 10 nm, or about 3 nm to 10 nm, or about 4 nm to 10 nm, or about 1 nm to 9 nm, or about 1 nm to 8 nm, or about 1 nm to 7 nm, or about 1 nm to 6 nm, or about 1 nm to 5 nm, or about 1 nm to 4 nm, or about 2 nm to 8 nm, or about 2 nm to 7 nm, or about 2 nm to 6 nm, or about 2 nm to 5 nm, or about 2 nm to 4 nm, or about 3 nm to 5 nm, wherein "particle size" refers to the average diameter of the substantially two-dimensional GQD. The emission spectrum of the GQD, including photoluminescence quantum yield decay lifetime, depends on the particle size of the GQD.

The GQD useful in the compositions and methods of the invention are made by either a "top down" or "bottom up" approach, as will be appreciated by one of skill. Top-down methods involve the decomposition and exfoliation of cheap, readily available bulk graphene-based materials, most commonly graphite, but require harsh conditions and often further require multiple steps involving concentrated acids, strong oxidizing agents, and high temperatures. A commonly employed top-down synthesis is called the Hummers method and involves exfoliation of graphite nanoparticles to form the single-layer GQD nanoparticles.

Bottom-up methods involve synthesis from polycyclic aromatic compounds or other molecules with aromatic structures such as fullerenes. Although complex, these methods allow for superior control of the properties and morphology of the final product compared to the top-down methods. In some of these methods, functional groups are added at the edge of the two-dimensional carbon "sheet" either inherently as part of the synthesis, or as a result of an extra step for this purpose. For example, Pan et al., *Adv. Mater.* 2010, 22, 734 employ hydrothermal cutting methodology involving an oxidation step in acidic conditions to result in development of epoxy moieties within a two-dimensional graphene sheet that ultimately are the sites of graphene sheet scission. The epoxy groups are further oxidized and yield carbonyl functionality at one or more sites present at the edges of the GQD formed by the scission process.

Other techniques to form functionalized GQD (GQD*) are known. Some representative currently known methods of GQD functionalization are discussed in Bacon, M. et al., *Part. Part. Syst. Charact.* 2014, 31, 415-428, which is incorporated by reference herein in its entirety. GQD useful in the invention are functionalized either during or after synthesis of the GQD. Useful herein are GQD "edge-functionalized" with carboxyl, hydroxyl, thiol, or amino functionality. At the time of this writing, carboxyl-functional GQDs are the most commonly available functionalized GQD. However, as techniques for edge-functionalized GQD are developed, Applicant expects additional options for covalently bonding CI compounds to GQD to become available. By way of non-limiting example, conjugation reactions using e.g. maleimide chemistry, so-called "click" chemistries, amide formation via N,N'-Dicyclohexylcarbodiimide (DCC) Coupling, and the like are possible chemistries useful in functionalizing GQD with PI. In this spirit, Applicant considers additional Gt-PI to fall within the scope of this disclosure as being equivalents of the presently disclosed Gt-PI structures. That is, Applicant discloses herein Gt-PI represented by the formula "GQD-[linking group]-PI" where a linking group is any chemical functionality formed by the reaction of a GQD* with a PI.

Useful GQD for the invention include amine-functionalized graphene quantum dots. The preparation of amine-functionalized graphene quantum dots is described in Jin et al., *Tuning the Photoluminescence of Graphene Quantum Dots through the Charge Transfer Effect of Functional Groups, ACS Nano* 2013, 7, 1239, which is incorporated by reference herein in its entirety. Amine-functionalized graphene quantum dots may be made by any of the top-down methods known in the art from amine-functionalized graphenes. The preparation of functionalized graphenes is described in US patent application publications 2011/0254432 and 2014/0121350, both of which are incorporated herein by reference in their entirety and for all purposes. Amine-functionalized graphene of flake size 0.5-5 microns is commercially available from the MKnano division of M K Impex Corporation, 6382 Lisgar Drive, Missisauga, ON L5N 6X1, Canada as product number MKN-SLG-NH2.

Attractive features or properties of GQD include the abundance of starting materials for synthesis thereof, non-toxicity of GQD, ease of preparation of GQD without relying on toxic precursors, the availability of edge-functionalized GQD for forming the Gt-PI, and the ability to control $\lambda$max by adjusting the size of the GQD to minimize overlap between $\lambda$max of crude oil and $\lambda$max of the Gt-PS. In many of these features or properties, GQD are preferable to organic-based fluorescent "tagging" compounds that are not environmentally friendly.

Conventional paraffin suppressant concentrates comprise, consist essentially of, or consist of a paraffin suppressant and one or more petroleum-based solvents, and optionally include a low-boiling co-solvent such as methanol, or a surfactant, or both. Paraffin inhibitors are useful as paraffin suppressants. Paraffin dispersants are useful as paraffin suppressants. Typically a paraffin inhibitor is a polymer such as a branched or comb-like polymer.

Paraffin inhibitors effective for suppressing paraffin deposition in crude oil include, e.g. ethylene polymers and copolymers thereof with vinyl acetate, acrylonitrile, or $\alpha$-olefins such as octene, butene, propylene, and the like; comb polymers with alkyl side chains such as methacrylate ester copolymers, maleic-olefinic ester copolymers, and maleic-olefinic amide copolymers; and branched copolymers having alkyl side chains such as alkylphenol-formaldehyde copolymers and polyethyleneimines.

One effective branched copolymer for suppressing paraffin deposition in crude oil comprises, consists of, or consists essentially of a copolymer comprising the residues of (i) an alpha olefin monomer and a maleic anhydride monomer or (ii) a maleic anhydride monomer and styrene. The alpha olefin monomer has the formula (I):

wherein $R_1$, $R_2$, $R_3$, and $R_4$ are independently selected from hydrogen and $C_5$-$C_{60}$ alkyl, with the proviso that at least two thereof are hydrogen; a blend of two or more such alpha olefin monomers having formula (I) are suitably included in the copolymer. In some embodiments $R_1$, $R_2$, $R_3$, and $R_4$ are independently hydrogen or $C_{12}$-$C_{60}$. The maleic anhydride monomer has the formula (II):

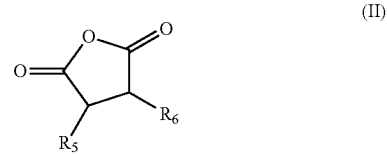

wherein $R_5$ and $R_6$ are independently hydrogen or alkyl. In some embodiments $R_5$ and $R_6$ are independently hydrogen or $C_{12}$-$C_{30}$.

In some embodiments, the copolymer of (I) and (II) is further reacted via the maleic anhydride residue with one or more alcohol or amine compounds to form the corresponding carboxylate or amide functionalities. In some such embodiments, the maleic anhydride residue is reacted with about 0.5 to 2.0 equivalents of the alcohol or amine per equivalent of anhydride. The alcohol or amine compounds are linear, branched, aromatic, or alkaromatic compounds having about 12 to 60 carbons. In embodiments, the amine or alcohol comprises, consists of, or consists essentially of a graphene quantum dot functionalized with amine and/or hydroxyl groups.

In some embodiments, the paraffin inhibitor comprises, consists of, or consists essentially of an ethylene-vinyl acetate copolymer.

In some embodiments, the paraffin inhibitor comprises, consists of, or consists essentially of an alkylphenol formaldehyde copolymer.

Several reaction schemes are shown in the Figures. It should be understood that there are many variations of the reaction schemes shown, as will be appreciated by one of skill.

FIG. 1 shows a general scheme for attaching a graphene quantum dot to a paraffin inhibitor to produce a graphene tagged paraffin inhibitor. The graphene tagged paraffin inhibitor is a conjugate of a residue of a functionalized graphene quantum dot and a residue of a paraffin inhibitor. A graphene quantum dot is functionalized by the addition of one or more first linking groups such as amino, carboxyl, hydroxyl, and the like to form the functionalized graphene quantum dot. The paraffin inhibitor comprises one or more second linking groups such as anhydride, carboxyl, amino, hydroxyl, formyl, and the like such that some or all of the one or more first linking groups disposed on the graphene quantum dot react with some or all of the second linking groups disposed on the paraffin inhibitor resulting in a residue of the paraffin inhibitor covalently bonded to the graphene quantum dot. In a non-limiting example, a graphene quantum dot functionalized with amine is reacted with an α-olefin/maleic anhydride copolymer—the amino group of the amine-functionalized graphene quantum dot reacts with the maleic anhydride residue of the copolymer resulting in a maleamic acid residue or a maleimide residue, and the copolymer residue is covalently bonded to the graphene quantum dot by an amic acid or maleimide residue respectively.

Alternatively, a functionalized graphene quantum dot as described above is reacted with a paraffin inhibitor premix (PI premix): the paraffin inhibitor premix comprises, consists of, or consists essentially of a mixture of compounds including a functionalized graphene quantum dot, wherein the PI premix is subjected to conditions suitable for phenol-formaldehyde condensation and therefore reacts to form a paraffin inhibitor, wherein some or all of the one or more first linking groups disposed on the graphene quantum dot react with one or more functional groups attached to other components of the paraffin inhibitor premix such that the graphene quantum dot is covalently bonded to a resultant paraffin inhibitor residue. In a non-limiting example, a paraffin inhibitor premix is made comprising an amine-functionalized graphene quantum dot, formaldehyde, and an alkylphenol. A polymeric condensation product results in which the graphene quantum dot is covalently bonded to a paraffin inhibitor residue comprising a phenol formaldehyde polymer with pendant alkyl groups.

A "functionalized GQD" is a GQD functionalized with a group capable of leaving readily under a broad range of conditions in favor of PI functionality or functionality capable of forming a Gt-PI. A PI, or a paraffin inhibitor premix capable of forming a PI, is reacted with the GQD-$NH_2$ or GQD* to result in a covalent bond between the GQD and the PI or PI-forming functionality. In some embodiments, one or more additional reactions are further carried out on the PI-forming functionality to form the Gt-PI; in other embodiments, the PI functionality is directly reacted with the GQD-$NH_2$ or GQD* to result in a Gt-PI.

Figure 2:
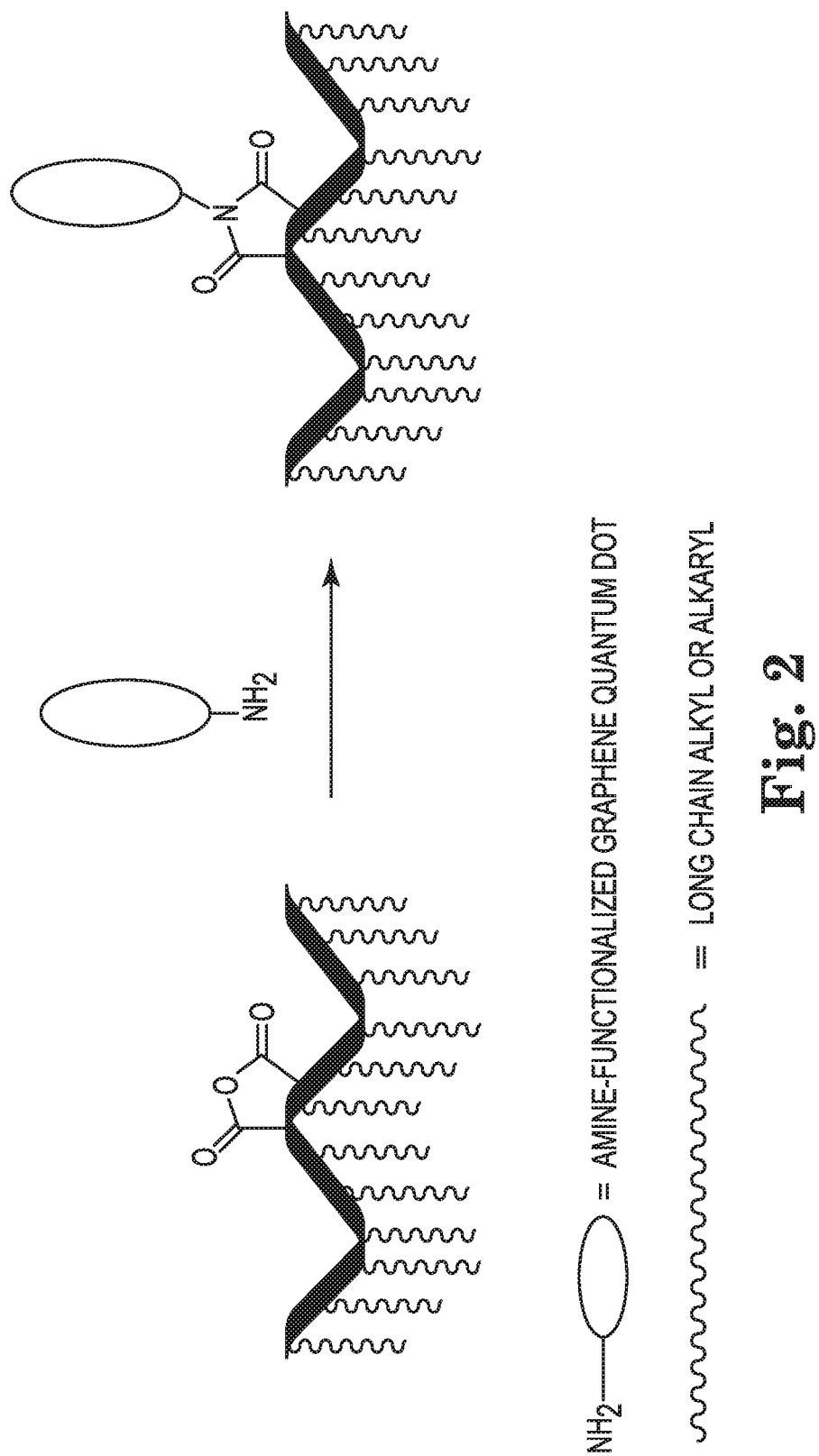
FIG. 2 illustrates a synthetic scheme for a graphene tagged paraffin inhibitor of the invention.

FIG. 2 shows another exemplary reaction scheme of the invention. Building on the reaction scheme involving amine-functionalization of the GQD to form a GQD*, FIG. 2 is a reaction scheme showing a GQD* reacted with a PI functionalized with a maleic anhydride residue (a substituted succinimide forming part of a polymer chain). The PI is a copolymer of maleic anhydride, thereby having anhydride functionality acting as second linking group capable of reaction with the amino group of the GQD*, shown to result in a Gt-PI. The Gt-PI therefore includes an imide group bonded to the GQD, the imide group forming an integral part of the residue of the PI. The maleimide residue is one example of an imide residue that is present in the PI residue; other imide residues such as nadimide are similarly useful as PI residues in the Gt-PI. Optionally, the Gt-PI is used in combination with one or more additional PI. The additional PI is tagged or untagged; the additional PI is a Gt-PI, a t-PI wherein the PI is covalently bonded to a moiety which is not a GQD but is capable of fluorescence, or a PI without a moiety capable of fluorescence attached thereto. In embodiments, the PI without a moiety capable of fluorescence attached thereto is the same PI as that reacted with the GQD* to form the Gt-PI, wherein the paraffin inhibitor is effective for suppressing paraffin deposition in crude oil.

Figure 3:
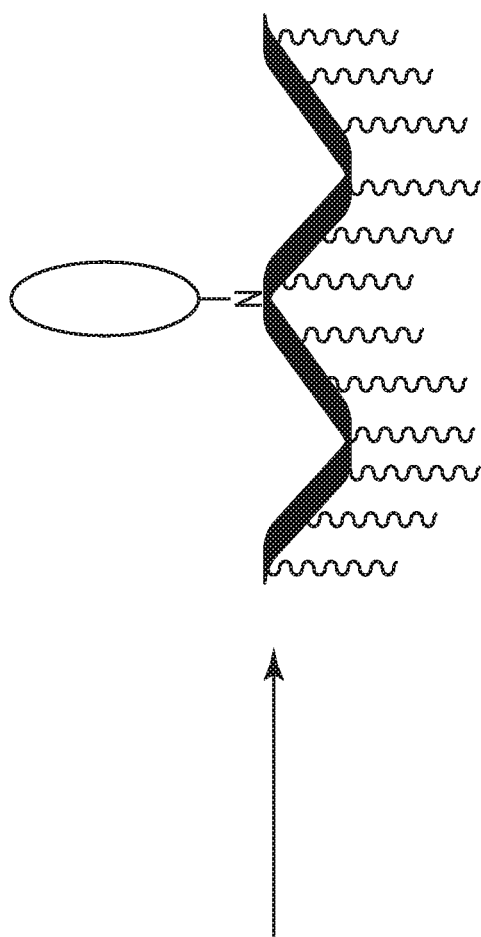
FIG. 3 illustrates a synthetic scheme for another graphene tagged paraffin inhibitor of the invention.
Figure 3:
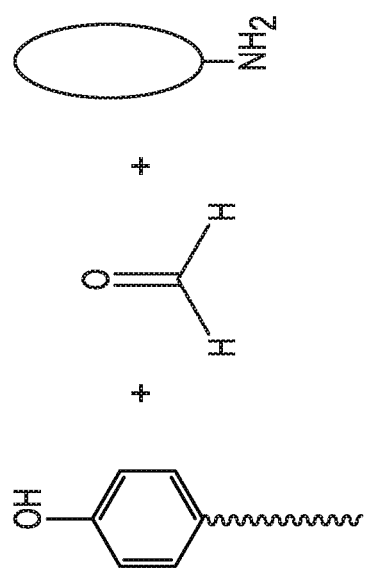

FIG. 3 shows another exemplary reaction scheme of the invention. FIG. 3 is a reaction scheme showing an amine-functionalized GQD (a GQD*) reacted with formaldehyde and a substituted phenol: the GQD*, formaldehyde, and substituted phenol form a PI premix which reacts to form a Gt-PI. Phenols condense with formaldehyde and primary or secondary amines to form—depending on starting materials, stoichiometry, reaction conditions, and/or other conditions such as solvent—aminoalkyl phenols, fusible polymers, infusible polymers, or mixtures thereof. When the amine employed is a primary amine, the aminoalkyl phenol contains an amino hydrogen that can participate in further condensation reactions yielding polymers. Such reactions and the conditions to control the products and yield fusible polymers are described in U.S. Pat. No. 3,436,373, which is incorporated herein by reference in its entirety and for all purposes. Other reaction conditions for forming phenolic resins may be found in U.S. Pat. No. 8,956,541, which is incorporated herein by reference in its entirety and for all purposes. In one embodiment, the PI premix is a composition comprising an amine-functionalized GQD; formaldehyde, and a substituted phenol having the formula

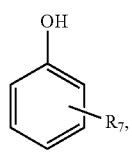

wherein the substituent $R_7$ is selected from the group consisting of $C_1$-$C_{60}$ alkyl and $C_1$-$C_{60}$ alkaryl. In one embodiment, $R_7$ is attached to the para position of the phenol. When subjected to suitable phenol-formaldehyde condensation conditions, the premix forms a Gt-PI. The Gt-PI includes an tertiary amine bonded to the graphene quantum dot and forming an integral part of the residue of the PI, as indicated schematically in FIG. 3.

Figure 4:
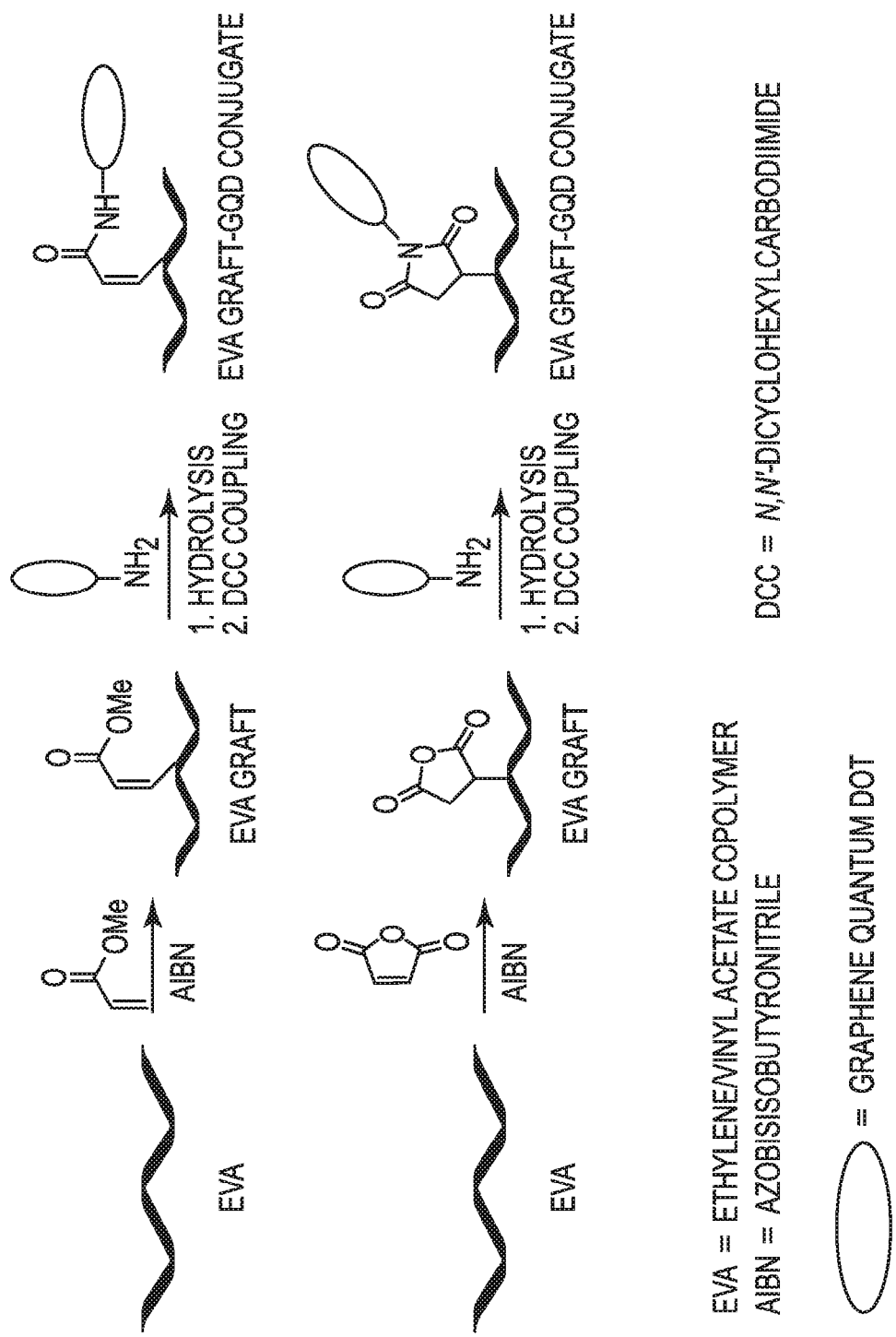
FIG. 4 illustrates a synthetic scheme for another graphene tagged paraffin inhibitor of the invention.

FIG. 4 shows another exemplary reaction scheme of the invention. FIG. 4 shows two exemplary schemes for attaching a graphene quantum dot to an ethylene-vinyl acetate copolymer to form another graphene tagged paraffin inhibitor of the invention. The first scheme shows the free-radical initiated addition of methyl acrylate to an ethylene-vinyl acetate copolymer, a paraffin inhibitor, to form an ethylene-vinyl acetate copolymer/acrylic ester graft. The graft can be hydrolyzed to the corresponding carboxylic acid, an ethylene-vinyl acetate copolymer/acrylic acid graft which can then be reacted with an amine-functionalized graphene quantum dot to form a graphene tagged paraffin inhibitor, wherein the graphene tagged paraffin inhibitor is an EVA graft-GQD conjugate comprising an amide linkage. Alternatively, the ethylene-vinyl acetate copolymer/acrylic ester graft can be reacted directly with the amine-functionalized graphene quantum dot to form the EVA graft-GQD conjugate comprising an amide linkage.

The second scheme shows the free-radical initiated addition of maleic anhydride to an ethylene-vinyl acetate copolymer, a paraffin inhibitor, to form ethylene-vinyl acetate copolymer/maleic acid graft. The graft is then reacted with an amine-functionalized graphene quantum dot to form an EVA graft-GQD conjugate comprising a maleimide linkage.

Figure 5:
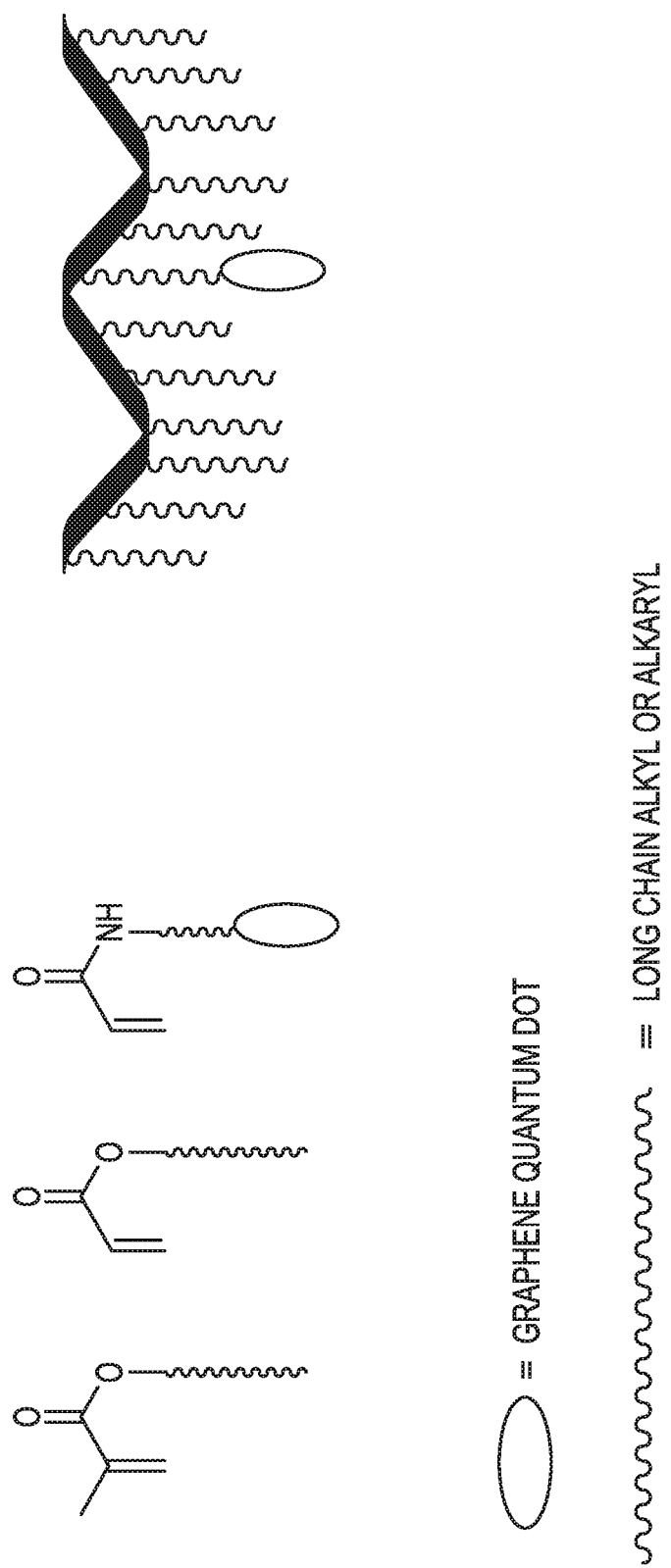
FIG. 5 illustrates a synthetic scheme for another graphene tagged paraffin inhibitor of the invention.

FIG. 5 shows another exemplary reaction scheme of the invention. FIG. 5 is an exemplary reaction scheme showing an acrylamido-functionalized GQD (a GQD*) reacted with a long-chain ester of acrylic acid and a long-chain ester of methacrylic acid: the GQD*, acrylic acid ester, and methacrylic acid ester form a PI premix which reacts to form a Gt-PI. Although FIG. 5 exemplifies three different unsaturated monomers, it will be appreciated that unsaturated monomers can be used providing that they will polymerize with each other to form a copolymer, that one monomer comprises a GQD covalently bound thereto, and that the resulting copolymer is effective as a PI.

Figure 6:
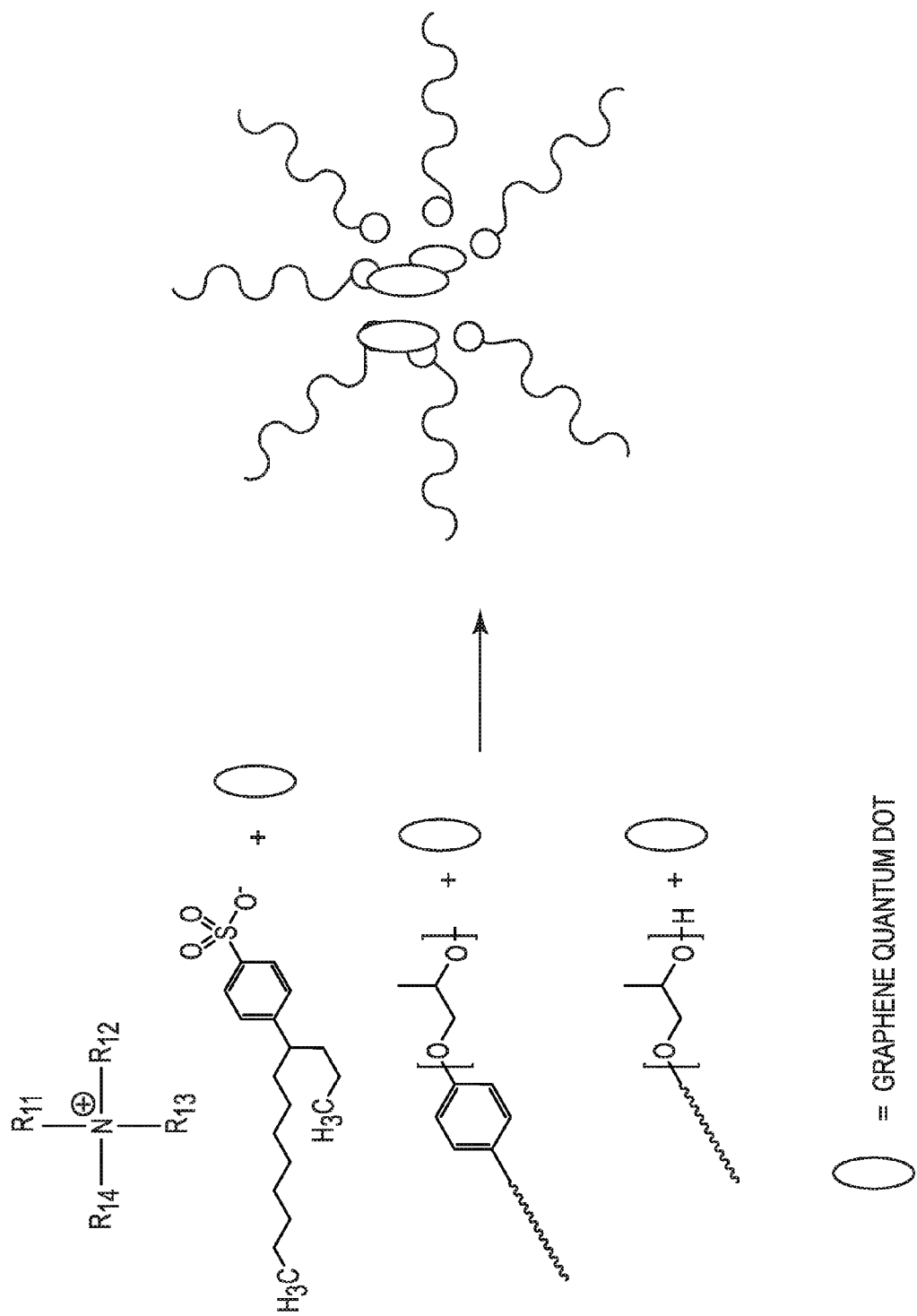
FIG. 6 illustrates a scheme for a graphene quantum dot tagged paraffin dispersant of the invention.

FIG. 6 shows a schematic of a further exemplary embodiment of the invention. FIG. 6 shows three exemplary dispersants with schematized exemplary ammonium counterion. In FIG. 6, the dispersants are paraffin dispersants which also function to disperse the graphene dot in a solvent. In FIG. 6, the graphene quantum dots are dispersed in inverse micelles.

In embodiments, there is provided a composition comprising, consisting of, or consisting essentially of a polymer, the polymer comprising, consisting of, or consisting essentially of a graphene quantum dot having a particle size of about 2 nm to 20 nm; and a residue of a paraffin inhibitor covalently bonded to the graphene quantum dot, wherein the residue of the paraffin inhibitor is effective for suppressing the phase separation of paraffin wax in crude oil. In embodiments, the residue of the paraffin inhibitor is a residue of a paraffin inhibitor known in the art. In embodiments, the paraffin inhibitor residue comprises, consists of, or consists essentially of an α-olefin monomer residue, maleimide residue, maleic anhydride residue, and/or maleamic acid residue. In embodiments, the α-olefin monomer residue comprises, consists of, or consists essentially of the residues of more than one type of α-olefin. In embodiments, the residues of more than one type of α-olefin are residues having different chain lengths from each other. In embodiments, the residues of more than one type of α-olefin are residues having similar or the same chain lengths as each other. In embodiments, the copolymer further comprises additional monomer residues selected from the residues of vinyl acetate, acrylic acid, methacrylic acid, a C1-C60 alkyl ester of acrylic acid, a C1-C60 alkyl ester of methacrylic acid, acrylonitrile, acrylamide, styrene, or a mixture thereof. In embodiments, the graphene quantum dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the paraffin inhibitor is entrained in an organic solvent to make a paraffin inhibitor concentrate. In embodiments, conventional paraffin inhibitor concentrates (PIC) comprise, consist essentially of, or consist of the paraffin inhibitor (PI) and one or more petroleum-based solvents, optionally including a low-boiling co-solvent such as methanol, or a surfactant, or both. In embodiments, the paraffin inhibitor concentrate is added to a crude oil, the paraffin inhibitor mixes with the crude oil, and the paraffin inhibitor thereby becomes entrained in the crude oil. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column. In other embodiments, the paraffin inhibitor is added directly to the crude oil. In embodiments, the paraffin inhibitor is effective for suppressing the phase separation of paraffin wax means that the residue of the paraffin inhibitor covalently bonded to the graphene quantum dot has about the same efficacy as substantially the same paraffin inhibitor without a quantum dot bonded thereto for inhibiting the phase separation of paraffin wax when added in the same crude oil at the same concentration under the same conditions. In embodiments, the conditions include temperature, time, the type of crude oil in which the paraffin inhibitor is entrained, and/or other conditions which are apparent to one of skill in the art. Substantially the same paraffin inhibitor without a quantum dot bonded thereto means the paraffin inhibitor without the graphene quantum dot bonded thereto and without minor differences between the paraffin inhibitor and the paraffin inhibitor residue in the graphene tagged paraffin inhibitor which differences provide a bond or bonds between the graphene quantum dot and the paraffin inhibitor residue.

First Embodiments

In first embodiments, there is provided a graphene tagged paraffin suppressant, wherein the suppressant is a polymer comprising a residue of an α-olefin having the formula (I)

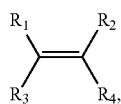

wherein $R_1$, $R_2$, $R_3$, and $R_4$ are independently selected from hydrogen and C5-C60 alkyl with the proviso that at least two thereof are hydrogen and at least one thereof is C5-C60 alkyl; and the residue of an imide having the formula (II)

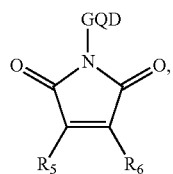

wherein GQD represents a graphene quantum dot having a particle size of about 2 nm to 20 nm covalently bonded to a nitrogen atom of the imide, and $R_5$ and $R_6$ are independently hydrogen or a C1-C30 alkyl. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm.

In embodiments, the graphene tagged paraffin suppressant is made by polymerizing together a mixture of one or more α-olefins, maleic anhydride, and optionally one or more additional unsaturated monomers to form an untagged suppressant; and adding an amino or hydroxy-functionalized graphene quantum dot and/or a composition comprising an amine or hydroxy-functionalized graphene quantum dot to form a mixture, and subjecting the mixture to heat and/or other conditions under which the functionalized graphene quantum dot reacts with the untagged suppressant to form the graphene tagged paraffin suppressant. In embodiments, the subjecting to heat and/or other conditions causes the amine or hydroxy functionality of the amine or hydroxy functionalized graphene quantum dot to react with the maleic anhydride residue of the untagged suppressant to form the tagged suppressant.

In embodiments, the one or more additional unsaturated monomers is selected from α-olefins, vinyl alkanoates, $C_1$-$C_{60}$ alkyl esters of acrylic acid, $C_1$-$C_{60}$ alkyl esters of methacrylic acid, citraconic anhydride, nadic anhydride, acrylamide, acrylonitrile, styrene, or mixtures thereof. In embodiments, the vinyl alkanoate is vinyl acetate. In embodiments, some or all of the olefins are α-olefins. In embodiments, $R_5$ and $R_6$ are both H. In embodiments, $R_5$ and $R_6$ are H and methyl. In embodiments, the graphene tagged paraffin suppressant is added to one or more organic solvents to form a paraffin suppressant concentrate. In embodiments, the one or more organic solvents, consists of, or consists essentially of a hydrocarbon solvent and optionally includes a low boiling cosolvent. In embodiments, the cosolvent is methanol or ethanol. In embodiments, the paraffin suppressant concentrate is added to an oil. In embodiments the oil is crude oil, and adding paraffin suppressant concentrate to the crude oil forms a graphene tagged crude oil composition. In embodiments, the graphene tagged paraffin suppressant is added to an oil. In embodiments the oil is crude oil, and adding the graphene tagged paraffin suppressant to the crude oil forms a graphene tagged crude oil composition. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the luminescent emission at λmax and/or the fluorescence spectrum of the graphene quantum dot of the paraffin suppressant is measured. The graphene quantum dot of a paraffin suppressant means the graphene quantum dot bonded to the residue of a paraffin inhibitor or the graphene quantum dot dispersed in an organic solvent by one or more paraffin dispersants. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Second Embodiments

In second embodiments there is provided a graphene tagged paraffin suppressant, wherein the suppressant is a polymer of an α-olefin having the formula (I)

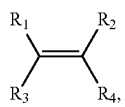

(I)

wherein $R_1$, $R_2$, $R_3$, and $R_4$ are independently selected from hydrogen and C5-C60 alkyl with the proviso that at least two thereof are hydrogen and at least one thereof is C5-C60 alkyl; and an imide having the formula (III)

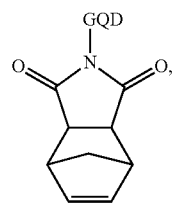

(III)

wherein GQD represents a graphene quantum dot having a particle size of about 2 nm to 20 nm covalently bonded to a nitrogen atom of the imide. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the suppressant is made by polymerizing together a mixture of one or more olefins, nadic anhydride, and optionally one or more additional unsaturated monomers. In embodiments, the one or more additional unsaturated monomers is selected from olefins, vinyl alkanoates, $C_1$-$C_{60}$ alkyl esters of acrylic acid, $C_1$-$C_{60}$ alkyl esters of methacrylic acid, citraconic anhydride, nadic anhydride, acrylamide, acrylonitrile, styrene, or mixtures thereof. In embodiments, the vinyl alkanoate is vinyl acetate. In embodiments, some or all of the olefins are α-olefins. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at λmax or some other specified wavelength or wavelengths, and/or the spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Third Embodiments

In third embodiments, there is provided a graphene tagged paraffin suppressant comprising a phenolic resin having a graphene quantum dot covalently bonded thereto. In embodiments, the graphene dot has a particle size of about 2 to about 20 nm, in embodiments, the graphene quantum dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments graphene tagged phenolic resin is synthesized by a method comprising: mixing an amine-functionalized graphene quantum dot, a phenolic resin, and optionally a solvent to form a mixture; and subjecting the mixture to conditions suitable for reacting the amine with the phenolic resin, wherein the graphene quantum dot becomes covalently bonded to the phenolic resin to form a graphene tagged paraffin suppressant. In embodiments, amine-functionalized graphene quantum dot is mixed with a phenol having the formula (IV)

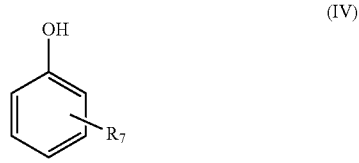

(IV)

wherein $R_7$ is selected from the group consisting of C5-C60 alkyl and C5-C60 alkaryl; formaldehyde; and optionally one or more additional comonomers selected from amines, aldehydes, and phenols. In embodiments, the phenols are selected from C5-C60 alkyl or C5-C60 alkaryl substituted cresols, catechols, resorcinols, hydroquinones, pyrogallols, phloroglucinols, salicylic acids, gallic acids, guaiacols, or mixtures thereof. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

In embodiments, samples are removed from the graphene tagged crude oil composition, and the fluorescent emission intensity at λmax or some other specified wavelength or wavelengths, and/or the spectrum of the graphene quantum dot of the paraffin suppressant is measured.

Fourth Embodiments

In fourth embodiments, there is provided a graphene tagged paraffin suppressant comprising a graphene quantum dot covalently bound to an ethylene-vinyl acetate copolymer by an alkylamide linkage. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the graphene quantum dot covalently bound to the ethylene-vinyl acetate copolymer by the alkylamide linkage has the formula (IX)

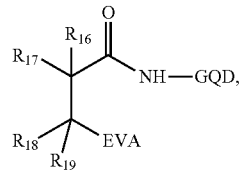

(IX)

wherein GQD represents the graphene quantum dot, EVA represents an ethylene-vinyl acetate copolymer, and —C($R_{18}$ $R_{19}$)C($R_{16}R_{17}$)(CO)NH— is an alkylamide linkage, and $R_{16}$, $R_{17}$, $R_{18}$, and $R_{19}$ are independently selected from hydrogen, alkyl, alkaryl, substituted alky, and substituted alkaryl. The alkylamide can be attached to the chain of the ethylene-vinyl acetate copolymer at any point where a free radical is formed on the ethylene-vinyl acetate copolymer by a free radical initiator and an acrylate adds to the ethylene-vinyl acetate copolymer chain. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at λmax and/or spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Fifth Embodiments

In fifth embodiments, there is provided a method making a graphene tagged paraffin suppressant, wherein the graphene tagged paraffin suppressant is a graphene tagged paraffin inhibitor, where the inhibitor is a polymer having the structure (IX). The method comprises: mixing a free radical initiator, methyl acrylate, an ethylene-vinyl acetate copolymer, and a solvent to form a mixture; heating or irradiating the mixture to initiate the free radical addition of the methyl acrylate to the ethylene-vinyl acetate copolymer to form a graft polymer, adding a catalyst or reactant such as an acid to hydrolyze the graft to the corresponding carboxylic acid, and adding to the mixture a an amine-functionalized graphene quantum dot to form a graphene tagged paraffin inhibitor having the structure (IX). In embodiments, the solvent is an organic solvent and the initiator, methyl acrylate, and ethylene-vinyl acetate copolymer are dissolved in the solvent. In some such embodiments the solvent is a hydrocarbon solvent. In embodiments the solvent is selected from toluene, benzene, xylene, methylene chloride, tetrahydrofuran, or 1-trichloroethane. In embodiments, the solvent is water and the ethylene-vinyl acetate copolymer and methyl acrylate are dispersed in the water with one or more surfactants.

In embodiments, there is provided a method of making a graphene tagged paraffin suppressant, wherein the graphene tagged paraffin suppressant is a graphene tagged paraffin inhibitor, where the inhibitor is a polymer having the structure (IX). The method comprises: mixing a free radical initiator, an acrylic acid, an ethylene-vinyl acetate copolymer, and a solvent to form a mixture; optionally heating or irradiating to initiate a free radical addition of the acrylic acid to the ethylene-vinyl acetate copolymer to form a carboxylic graft; and adding to the corresponding carboxylic graft an amine-functionalized graphene quantum dot to form a graphene tagged paraffin inhibitor having the structure (IX). In embodiments, the solvent is an organic solvent and the initiator, methyl acrylate, and ethylene-vinyl acetate copolymer are dissolved in the solvent. In some such embodiments the solvent is a hydrocarbon solvent. In embodiments the solvent is selected from toluene, benzene, xylene, methylene chloride, tetrahydrofuran, or 1-trichloroethane. In embodiments, the solvent is water and the ethylene-vinyl acetate copolymer and methyl acrylate are dispersed in the water with one or more surfactants.

Sixth Embodiments

In sixth embodiments, there is provided a method of making a graphene tagged paraffin suppressant, wherein the graphene tagged paraffin suppressant is a graphene tagged paraffin inhibitor, where the inhibitor is a polymer having the structure (IX). The method comprises: mixing a free radical initiator, methyl acrylate, an ethylene-vinyl acetate copolymer, and a solvent to form a mixture, optionally heating and/or irradiating to initiate addition of the methyl acrylate to the ethylene vinyl acetate copolymer to form a graft, and adding an amine-functionalized graphene quantum dot to the mixture to form a graphene tagged paraffin inhibitor having the structure (IX). In embodiments, the solvent is an organic solvent and the initiator, methyl acrylate, and ethylene-vinyl acetate copolymer are dissolved in the solvent. In some such embodiments the solvent is a hydrocarbon solvent. In embodiments the solvent is selected from toluene, benzene, xylene, methylene chloride, tetrahydrofuran, or 1-trichloroethane. In embodiments, the solvent is water and the ethylene-vinyl acetate copolymer and methyl acrylate are dispersed in the water with one or more surfactants.

Seventh Embodiments

In seventh embodiments, there is provided a method of making a graphene tagged paraffin suppressant mix comprising: composing an imide premix comprising an amine functionalized graphene quantum dot, optionally one or more long-chain amines, and an anhydride selected from maleic anhydride, citraconic anhydride, nadic anhydride, or combinations thereof; subjecting the imide premix to conditions under which the amine including the amine functionalized graphene quantum dot reacts with the anhydride to form an imide mixture; combining the imide mixture with one or more α-olefins to form a polymer premix, and polymerizing the polymer premix to form the graphene tagged paraffin suppressant mix. Herein, "polymerizing" a composition such as a premix or a mixture means subjecting the composition to conditions under which the monomers in the composition react with each other to form a polymer. In embodiments, the conditions under which the monomers in the composition react with each other to form a polymer are selected from mixing, applying heat, adding a free-radical initiator, adding an ionic initiator, adding a catalyst, adding a solvent, or combinations thereof. In embodiments, the long chain amine is C1 to C50 alkyl amine, C1-C50 aryl amine, C1 to C50 aralkyl amine. In embodiments, the alkyl is linear alkyl, branched alkyl, alicyclic alkyl, or a combinations thereof. In embodiments, the long-chain amine is a fatty acid amine. In embodiments, the long chain amine is selected from hydrogenated tallow amine, stearyl amine, or a combination thereof. In embodiments, the molar ratio of amine functionalized graphene quantum dot to long chain amine is 1:99 to 10:90. In embodiments, the weight ratio of amine functionalized graphene quantum dot to long chain amine is 0.01:99.99 to 10:90, in embodiments 0.05:99.95 to 10:90, in embodiments 0.1:99.9 to 10:90, in embodiments 0.5:99.5 to 10:90, in embodiments 0.75:99.25 to 10:90, in embodiments 1:99 to 10:90. Advantageously, the ratio of amine functionalized graphene quantum dot to long chain amine can be varied to control the degree of fluorescence of the graphene tagged paraffin suppressant mix. In embodiments, the graphene tagged paraffin suppressant mix is combined with one or more solvents to form a paraffin suppressant concentrate. In embodiments, the paraffin suppressant mix and/or the paraffin suppressant concentrate is added to a composition comprising, consisting of, or consisting essentially of crude oil.

Eighth Embodiments

In eighth embodiments, there is provided a graphene tagged paraffin suppressant having the structure (XI)

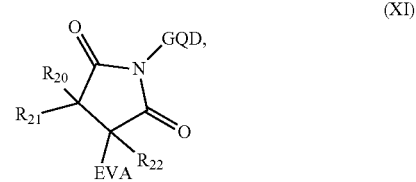

wherein GQD represents the graphene quantum dot, EVA represents an ethylene-vinyl acetate copolymer, and $R_{20}$, $R_{21}$, and $R_{22}$ are independently selected from hydrogen, alkyl, alkaryl, substituted alkyl, or substituted alkaryl. $R_{20}$, $R_{21}$, and $R_{22}$ can include long chains including polymers. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at λmax or some other specified wavelength or wavelengths, and/or the spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Ninth Embodiments

In ninth embodiments, there is provided a method making a graphene tagged paraffin suppressant, wherein the graphene tagged paraffin suppressant is a graphene tagged paraffin inhibitor, where the inhibitor is a polymer having the structure (XI). The method comprises: mixing a free radical initiator, maleic anhydride or a substituted maleic anhydride, an ethylene-vinyl acetate copolymer, and a solvent to form a mixture; optionally heating or irradiating the mixture to initiate the addition of the maleic anhydride or the substituted maleic anhydride to the ethylene-vinyl acetate copolymer to form a graft, and adding to the mixture an amine-functionalized graphene quantum dot to form a graphene tagged paraffin inhibitor having the structure (XI).

Tenth Embodiments

In tenth embodiments there is provided a paraffin inhibitor premix comprising: an amine-functionalized graphene quantum dot having a particle size of about 2 nm to 20 nm covalently bonded to the nitrogen atom of the amino group; a substituted phenol having the formula (IV)

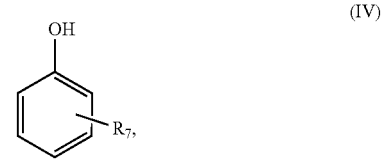

wherein $R_7$ is selected from the group consisting of C5-C60 alkyl and C5-C60 alkaryl; and formaldehyde. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the premix is reacted to form a graphene tagged paraffin suppressant, wherein the graphene tagged paraffin suppressant comprises, consists of, or consists essentially of a phenol-formaldehyde resin with a graphene quantum dot bound thereto. In embodiments, the method comprises mixing the phenol, the amine-functionalized graphene quantum dot, and formaldehyde to form a mixture and subjecting the mixture to conditions suitable for phenol-formaldehyde condensation. In embodiments, the mixture further comprises one or more solvents. In embodiments, the conditions do not produce an insoluble infusible resin. The proportions of the phenol, formaldehyde, and the amine-functionalized graphene quantum dot can vary over a fairly wide range. For example, the molar proportion of the phenol(formaldehyde plus amine) can vary from about 0.6:1 to about 3.3:1, and preferably from about 0.7:1 to about 2:1. The molar proportions of the formaldehyde to amine (i.e. formaldehyde to amine groups) can vary from about 0.75:1 to about 3:1, and is preferably from about 1:1 to about 2:1. The above proportions are appropriate for primary-amine functionalized graphene quantum dots. In embodiments, the graphene tagged paraffin suppressant is produced by slowly adding formaldehyde or a composition comprising formaldehyde to an agitated mixture of the phenol and the amine-functionalized graphene quantum dot to form the premix. In embodiments, the composition comprising the formaldehyde comprises, consists essentially of, or consists of formaldehyde and one or more solvents. In embodiments, the agitated mixture of the phenol and the graphene quantum dot further comprises one or more solvents. The addition period is followed by a reaction period. In embodiments, the formaldehyde addition and subsequent reaction is carried out at a temperature below the temperature at which the formaldehyde, functionalized quantum dot, and the phenol polymerizes to an insoluble infusible polymer. In embodiments the reaction is carried out at or below 110° C. In embodiments, the reaction is carried out at between 5° C. and 110° C., in embodiments the reaction is carried out between 25° C. and 100° C. In embodiments, the formaldehyde is added over 30 minutes to ten hours. In embodiments, the one or more solvents is selected from methanol, tetrahydrofuran, isopropanol, dioxane, or a mixture thereof. The time, temperature, the use of a solvent and which solvent, and the exact order of mixing, and addition rate of the ingredients can be adjusted by routine experimentation depending on the specific reactants, solvents, and other factors which will be routine to one of ordinary skill in the art.

In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at λmax or some other specified wavelength or wavelengths, and/or the spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Eleventh Embodiments

In eleventh embodiments, there is provided a paraffin inhibitor premix comprising: an unsaturated monomer having the formula (V)

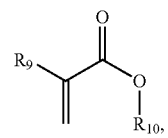

(V)

wherein $R_9$ is hydrogen or methyl, and $R_{10}$ is a C5-C60 alkyl or alkaryl; and an acrylamido functionalized graphene quantum dot (GQD) having the formula (VI)

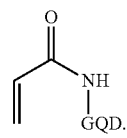

(VI)

In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the premix is reacted to form a graphene tagged paraffin suppressant, wherein the graphene tagged paraffin suppressant comprises, consists of, or consists essentially of an acrylic polymer with a graphene quantum dot bound thereto. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at max or some other specified wavelength or wavelengths, and/or the spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Twelfth Embodiments

In twelfth embodiments, there is provided a paraffin inhibitor premix comprising one or more unsaturated monomers selected from the group consisting of ethylene, maleic acid, a maleimide, vinyl acetate, acrylonitrile, styrene, an α-olefin, and mixtures thereof, wherein the α-olefin has the formula (I)

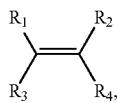

(I)

wherein $R_1$, $R_2$, $R_3$, and $R_4$ are independently selected from hydrogen and C5-C60 alkyl with the proviso that at least two thereof are hydrogen and at least one thereof is C5-C60 alkyl; and an acrylamido functionalized graphene quantum dot having the formula (VI)

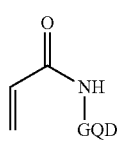

(VI)

wherein GQD represents a graphene quantum dot covalently bonded to the nitrogen atom of the acrylamido group. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the premix is reacted to form a graphene tagged paraffin suppressant, wherein the graphene tagged paraffin suppressant comprises, consists of, or consists essentially of an acrylic polymer with a graphene quantum dot bound thereto. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at λmax or some other specified wavelength or wavelengths, and/or the spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Thirteenth Embodiments

In thirteenth embodiments, there is provided a graphene tagged paraffin suppressant made by reacting a premix to form a residue of a paraffin inhibitor covalently bonded to the graphene quantum dot. "Reacting a premix" herein means that conditions are provided to the premix that allow monomers present in the premix to react with each other to form a polymer. In embodiments, the conditions are an increase in temperature; addition of a catalyst such as an acidic material, a basic material, one or more cations, one or more anions, a free-radical initiator; or another condition known by one of skill; or more than one thereof, the conditions being applied to the premix as appropriate and obvious to one of skill. In embodiments, the paraffin inhibitor premix comprises, consists of, or consists essentially of an amine-functionalized graphene quantum dot having a particle size of about 2 nm to 20 nm covalently bonded to the nitrogen atom of the amino group; a substituted phenol having the formula (IV)

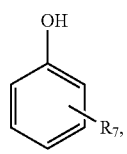

(IV)

wherein $R_7$ is selected from the group consisting of C5-C60 alkyl and C5-C60 alkaryl; and formaldehyde. In further embodiments, the paraffin inhibitor premix comprises an unsaturated monomer having the formula (V)

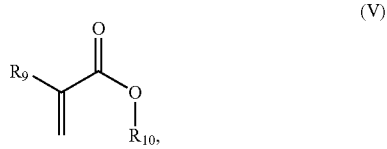

wherein $R_9$ is hydrogen or methyl, and $R_{10}$ is a C5-C60 alkyl or alkaryl; and an acrylamido functionalized graphene quantum dot (GQD) having the formula (VI)

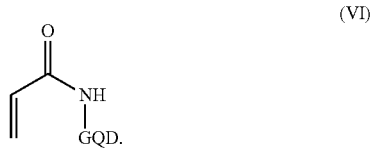

In further embodiments, the premix comprises, consists of, or consists essentially of one or more unsaturated monomers selected from the group consisting of ethylene, maleic acid, a maleimide, vinyl acetate, acrylonitrile, styrene, an α-olefin, and mixtures thereof, wherein the α-olefin has the formula (I)

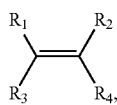

wherein $R_1$, $R_2$, $R_3$, and $R_4$ are independently selected from hydrogen and C5-C60 alkyl with the proviso that at least two thereof are hydrogen and at least one thereof is C5-C60 alkyl; and an acrylamido functionalized graphene quantum dot having the formula (VI)

wherein GQD represents a graphene quantum dot covalently bonded to the nitrogen atom of the acrylamido group. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the premix is reacted to form a graphene tagged paraffin suppressant, wherein the graphene tagged paraffin suppressant comprises, consists of, or consists essentially of an acrylic polymer with a graphene quantum dot bound thereto. In embodiments, the graphene tagged paraffin suppressant is entrained in one or more organic solvents to form a paraffin suppressant concentrate.

In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column. In embodiments, samples are removed from the graphene tagged crude oil composition, and the fluorescent emission intensity at λmax or some other specified wavelength or wavelengths, and/or the spectrum of the graphene quantum dot of the paraffin suppressant is measured.

Fourteenth Embodiments

In fourteenth embodiments, there is provided a graphene tagged paraffin suppressant comprising a graphene quantum dot; one or more paraffin dispersants; and a hydrophobic liquid, wherein the one or more paraffin dispersants forms inverse micelles with the graphene quantum dot and the graphene quantum dot is dispersed in the hydrophobic liquid. In embodiments, the hydrophobic liquid comprises one or more solvents. In embodiments the one or more solvents comprises a hydrocarbon solvent. In embodiments, the one or more solvents comprises a hydrocarbon solvent and an alcohol. In embodiments, the alcohol is selected from ethanol, methanol, and mixtures thereof. In embodiments, the hydrocarbon is selected from aromatic hydrocarbons selected from toluene, benzene, xylene, light aromatic naphtha, heavy aromatic naphtha, or mixtures thereof; kerosene; diesel; one or more linear or branched alkanes selected from pentanes, heptanes, hexanes, octanes, nonanes, decanes, undecanes, dodecanes, tridecanes, tetradecanes, pentadecanes, hexadecanes, or mixtures thereof; cycloalkane isomers of the one or more linear or branched alkanes; or mixtures thereof. One non-limiting example of an inverse micelle of the invention is represented schematically in FIG. 6. Each of the inverse micelles comprises, consists of, or consists essentially of one or more graphene quantum dots surrounded by molecules of one or more paraffin dispersants, wherein the molecules of the one or more paraffin dispersants each possess a relatively polar head group, which in some embodiments is ionic, and a hydrophobic section or hydrophobic tail. The relatively polar head groups of the one or more paraffin dispersants associate with the one or more graphene quantum dots in the interior of the inverse micelles, whereas the tails of the one or more paraffin dispersants tails extend out towards or into the hydrophobic liquid. In embodiments, the one or more paraffin dispersants is selected from the group consisting of an ammonium salt of a long-chain alkyl benzene sulfonic acid, an alkoxylated long-chain alkyl phenol, an alkoxylated long-chain alcohol, and mixtures thereof. In embodiments, the ammonium is $NH_4^+$, primary ammonium, secondary ammonium, tertiary ammonium, or mixtures thereof. In embodiments, the ammonium is represented by the formula (X)

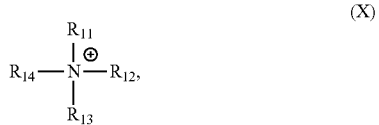

wherein $R_{11}$, $R_{12}$, $R_{13}$, and $R_{14}$ are individually selected from hydrogen, alky, aryl, or alkaryl. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the graphene tagged paraffin suppressant is entrained in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, the graphene tagged paraffin suppressant is entrained in an oil. In embodiments the oil is crude oil, and adding the graphene tagged paraffin suppressant to the crude oil forms a graphene tagged crude oil composition. In embodiments, samples are removed from the graphene tagged crude oil composition, and the fluorescent emission intensity at λmax or some other specified wavelength or wavelengths, and/or the spectrum of the graphene quantum dot of the paraffin suppressant is measured. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Fifteenth Embodiments

In fifteenth embodiments, there is provided a composition comprising crude oil; and any of the graphene tagged suppressants described herein, wherein the total concentration of the paraffin suppressant plus the graphene quantum dot in the crude oil is about 5 ppm to 5000 ppm by weight. In embodiments, the composition comprising crude oil further comprises one or more organic solvents. In embodiments, the one or more organic solvents include at least one hydrocarbon solvent. In embodiments, the one or more organic solvents comprises at least one hydrocarbon solvent and a low boiling organic solvent. In embodiments, the low boiling organic solvent is methanol or ethanol. In embodiments, the composition comprising crude oil further comprises, consists of, or consists essentially of a second paraffin suppressant selected from the group consisting of an α-olefin-maleic anhydride copolymer, an ethylene-vinyl acetate copolymer, a long-chain acrylic polymer, a long-chain-alkyl phenol-formaldehyde resin, an alkoxylated long-chain-alkyl phenol, an alkoxylated long-chain alcohol, an ammonium salt of a long-chain-alkyl benzene sulfonate, and mixtures thereof.

Sixteenth Embodiments

In sixteenth embodiments, there is provided a method of making a graphene tagged paraffin inhibitor comprising: mixing a functionalized graphene quantum dot having a particle size of about 2 nm to 20 nm and having one or more graphene functional groups attached thereto with a paraffin inhibitor, wherein the paraffin inhibitor has one or more paraffin inhibitor functional groups which react with the one or more graphene functional groups to form a graphene tagged paraffin inhibitor wherein the quantum dot is covalently bound to a residue of the paraffin inhibitor. In embodiments, the one or more graphene functional groups is selected from amine, hydroxy, carboxy, carboxylate, carboxylic acid ester, or combinations thereof. In embodiments, the one or more paraffin inhibitor functional groups is selected from carboxy, carboxylate, hydroxyl, amine, carboxylic anhydride, or combinations thereof. It will be appreciated by one of skill in the art that the combination of the one or more graphene functional groups and the one or more paraffin inhibitor functional groups is selected such that the one or more graphene functional groups is reactive with the one or more paraffin inhibitor functional groups such that the result is a single linking group which provides a covalent bond between the functionalized graphene quantum dot and the paraffin inhibitor residue. In embodiments, the one or more graphene functional groups is amine, and the one more paraffin inhibitor functional groups is selected from the group consisting of anhydride, carboxylate, carboxylic acid, carboxylic acid ester, and mixtures thereof. In embodiments, the paraffin inhibitor is a copolymer of maleic anhydride and an α-olefin. In embodiments, the paraffin inhibitor is a polymer of nadic anhydride and an α-olefin. In embodiments, the α-olefin has the formula (I)

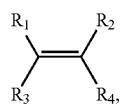

(I)

wherein $R_1$, $R_2$, $R_3$, and $R_4$ are independently selected from hydrogen and C5-C60 alkyl with the proviso that at least two thereof are hydrogen and at least one thereof is C5-C60 alkyl. In embodiments, the paraffin inhibitor is a polymer of nadic anhydride and an α-olefin. In embodiments, the α-olefin has the formula (I). In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, a method of tracing a paraffin inhibitor comprises the method of making the graphene tagged paraffin inhibitor, and entraining the graphene tagged paraffin inhibitor in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, a second method of tracing a paraffin inhibitor comprises, consists of, or consists essentially of the making the graphene tagged paraffin inhibitor, entraining the graphene tagged paraffin inhibitor in an oil. In embodiments the oil is crude oil, and entraining the graphene tagged paraffin suppressant in the crude oil forms a graphene tagged crude oil composition. In embodiments, the method further comprises removing samples from the graphene tagged crude oil composition, and measuring fluorescent emission intensity at the λmax of the paraffin inhibitor. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Seventeenth Embodiments

In seventeenth embodiments, there is provided a method of making a paraffin suppressant comprising: optionally adding a solvent to a paraffin inhibitor premix comprising a functionalized graphene quantum dot having a particle size of about 2 nm to 20 nm and one or more co-monomers to form a mixture, and heating the mixture. In embodiments, the one or more comonomers comprises, consists of, or consists essentially of: a long chain substituted phenol having the formula (IV)

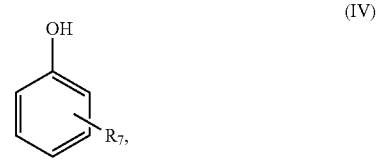

(IV)

wherein $R_7$ is selected from the group consisting of C5-C60 alkyl and C5-C60 alkaryl; and formaldehyde. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the method comprises mixing the phenol, the amine-functionalized graphene quantum dot, and formaldehyde to form a mixture and subjecting the mixture to conditions suitable for phenol-formaldehyde condensation. In embodiments, the mixture further comprises one or more solvents. The proportions of the phenol, formaldehyde, and the amine-functionalized graphene quantum dot can vary over a fairly wide range. For example, the molar proportion of the phenol:(formaldehyde plus amine) can vary from about 0.6:1 to about 3.3:1, and preferably from about 0.7:1 to about 2:1. The molar proportions of the formaldehyde to amine (i.e. formaldehyde to amine groups) can vary from about 0.75:1 to about 3:1, and is preferably from about 1:1 to about 2:1. The above proportions are appropriate for primary-amine functionalized graphene quantum dots. In embodiments, the graphene tagged paraffin suppressant is produced by slowly adding formaldehyde or a composition comprising formaldehyde to an agitated mixture of the phenol and the amine-functionalized graphene quantum dot to form the premix. In embodiments, the composition comprising the formaldehyde comprises, consists essentially of, or consists of formaldehyde and one or more solvents. In embodiments, the agitated mixture of the phenol and the graphene quantum dot further comprises one or more solvents. The addition period is followed by a reaction period. In embodiments, the formaldehyde addition and subsequent reaction is carried out at a temperature below the temperature at which the formaldehyde, functionalized quantum dot, and the phenol polymerizes to an insoluble infusible polymer. In embodiments the reaction is carried out at or below 110° C. In embodiments, the reaction is carried out at between 5° C. and 110° C., in embodiments the reaction is carried out between 25° C. and 100° C. In embodiments, the formaldehyde is added over 30 minutes to ten hours. In embodiments, the one or more solvents is selected from methanol, tetrahydrofuran, isopropanol, dioxane, or a mixture thereof. The time, temperature, the use of a solvent and which solvent, and the exact order of mixing, and addition rate of the ingredients can be adjusted by routine experimentation depending on the specific reactants, solvents, and other factors which will be routine to one of ordinary skill in the art.

Eighteenth Embodiments

In eighteenth embodiments, a method of tracing a paraffin inhibitor comprises, consists of, or consists essentially of the method of making the graphene tagged paraffin inhibitor, and entraining the graphene tagged paraffin inhibitor in one or more organic solvents to form a paraffin suppressant concentrate. In embodiments, the one or more organic solvents is selected from hydrocarbon solvents, alcohols, and ketones. In embodiments, the one or more organic solvents comprises, consists of, or consists essentially of a hydrocarbon solvent and optionally includes a low boiling cosolvent. In embodiments, the cosolvent is methanol or ethanol. In embodiments, the paraffin suppressant concentrate is entrained in an oil. In embodiments the oil is crude oil, and adding paraffin suppressant concentrate to the crude oil forms a graphene tagged crude oil composition. In embodiments, a second method of tracing a paraffin inhibitor comprises, consists of, or consists essentially of the making the graphene tagged paraffin inhibitor and entraining the graphene tagged paraffin inhibitor in an oil. In embodiments the oil is crude oil, and entraining the graphene tagged paraffin suppressant in the crude oil forms a graphene tagged crude oil composition. In embodiments, the method further comprises removing samples from the graphene tagged crude oil composition, and measuring the fluorescent emission intensity at λmax of the paraffin inhibitor. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Nineteenth Embodiments

In nineteenth embodiments, there is provided a method of making a graphene tagged paraffin inhibitor comprising grafting an acrylic ester having the formula (VII)

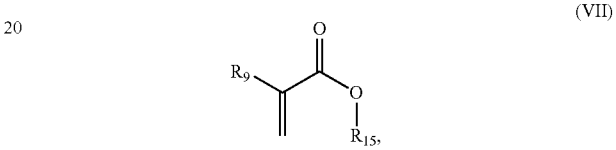

(VII)

wherein $R_9$ is selected from the group consisting of hydrogen and methyl, and $R_{15}$ is a C1-C5 alkyl, to an ethylene-vinyl acetate copolymer using a free-radical initiator to form a grafted polymer (an ethylene-vinyl acetate copolymer/acrylic ester graft); hydrolyzing the grafted polymer to form a hydrolyzed grafted polymer (an ethylene-vinyl acetate copolymer/acrylic acid graft); and reacting the hydrolyzed grafted polymer with an amine-functionalized graphene quantum dot to form a graphene tagged paraffin inhibitor. Hydrolyzing the grafted polymer means hydrolyzing —($R_9$)C—(C=O)—$OR_{15}$ group to a —($R_9$)C—(C=O)—OH carboxylic group or the conjugate base of a —($R_9$)C—(C=O)—OH carboxylic group. In embodiments, the initiator is selected from azo compounds, peroxides, persulfates, or mixtures thereof. In embodiments, the free radical initiator is selected from azobisisobutyronitrile, benzoyl peroxide, dicumyl peroxide, a persulfate, or mixtures thereof. The reaction can be conducted by means known to one of ordinary skill in the art. In embodiments, the grafting is conducted in solution. In embodiments, the solution is a solution of reactants comprising the ethylene-vinyl acetate copolymer, the acrylic ester, and the initiator. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. The reacting the hydrolyzed grafted polymer with an amine-functionalized graphene quantum dot to form a graphene-tagged paraffin inhibitor means reacting the —($R_9$)C—(C=O)—OH carboxylic group or the conjugate base of the —($R_9$)C—(C=O)—OH carboxylic group with the amine group of the amine-functionalized graphene quantum dot ($H_2$N-GQD) to form a group having the formula —$R_9$C—(C=O)—O—N(H)-GQD.

Twentieth Embodiments

In twentieth embodiments, there is provided a method of making a graphene tagged paraffin inhibitor comprising grafting an acrylic compound having the formula (VII)

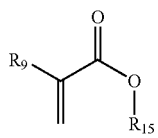

(VII)

wherein R₉ is selected from the group consisting of hydrogen and methyl, and R₁₅ is hydrogen or a C1-C5 alkyl to an ethylene-vinyl acetate copolymer using a free-radical initiator to form a grafted polymer (an ethylene-vinyl acetate copolymer/acrylic graft); and reacting the grafted polymer with an amine-functionalized graphene quantum dot to form a graphene tagged paraffin suppressant. In embodiments, R₁₅ is methyl and R₉ is hydrogen. In embodiments, each of R₁₅ and R₉ is hydrogen. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm. In embodiments, the initiator is selected from azo compounds, peroxides, persulfates, or mixtures thereof. In embodiments, the free radical initiator is selected from azobisisobutyronitrile, benzoyl peroxide, dicumyl peroxide, a persulfate, or mixtures thereof. The reaction can be conducted by means known to one of ordinary skill in the art. In embodiments, the grafting is conducted in solution. In embodiments, the solution is a solution of reactants comprising the ethylene-vinyl acetate copolymer, the acrylic ester, and the initiator.

Twenty-First Embodiments

In twenty-first embodiments, there is provided a method of making a graphene tagged paraffin inhibitor comprising grafting a maleic anhydride to an ethylene-vinyl acetate copolymer using a free-radical initiator to form an ethylene-vinyl acetate copolymer/maleic anhydride graft; and reacting the ethylene-vinyl acetate copolymer/maleic anhydride graft with an amine-functionalized graphene quantum dot to form an EVA graft-GQD conjugate comprising a maleimide linkage. In embodiments, the maleic anhydride is a substituted maleic anhydride having the formula (II)

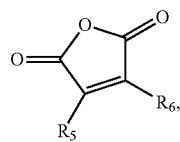

(II)

wherein R₅ and R₆ are both hydrogen, or R5 is hydrogen and R6 is methyl. In embodiments, the graphene dot has a particle size of about 5 to about 15 nm; in embodiments, about 2 to about 5 nm; in embodiments, about 5 to about 10 nm; in embodiments, about 10 to about 15 nm; in embodiments, about 15 nm to about 20 nm.

Twenty-Second Embodiments

In twenty-second embodiments, there is provided a method of making a graphene tagged crude oil composition, the method comprising entraining any of the graphene tagged paraffin suppressants or graphene tagged paraffin inhibitors described herein in one or more organic solvents to form a graphene tagged paraffin suppressant concentrate; and adding the graphene tagged paraffin suppressant concentrate to crude oil. In embodiments, the one or more organic solvents comprises, consists of, or consists essentially of one or more hydrocarbon solvents. In embodiments, the one or more organic solvents comprises, consists of, or consists essentially of one or more hydrocarbon solvents and one or more low boiling solvents. In some embodiments, the paraffin inhibitor suppressant concentrate is added to crude oil in an oil extraction process, wherein oil is extracted from a subterranean oil reservoir in, for example, an oil field. In some embodiments, the oil extraction process is an enhanced oil recovery process selected from fracking or gas lift oil recovery. In some embodiments, the paraffin inhibitor suppressant concentrate is added to crude oil in a subterranean reservoir. In some embodiments, the paraffin inhibitor concentrate is added to the crude oil after the crude oil emerges from the subterranean reservoir. In some embodiments, the paraffin inhibitor suppressant concentrate is added to the crude oil below ground. In some embodiments, the paraffin inhibitor suppressant concentrate is added to the crude oil above ground. In some embodiments, the paraffin inhibitor suppressant concentrate is added to the crude oil by introducing the concentrate into the crude oil via a capillary string. In some embodiments, the paraffin inhibitor suppressant concentrate is added to the crude oil via an annulus of a downpipe which is in communication with a subterranean oil reservoir. In some embodiments, the paraffin inhibitor suppressant concentrate is added to crude oil in an oil processing operation such as oil refining and the like.

In some embodiments, the paraffin inhibitor suppressant concentrate is added to crude oil in an oil transportation process such as transportation of oil by oil pipeline. In some embodiments, the paraffin inhibitor suppressant concentrate is added to crude oil in an oil storage process. The paraffin inhibitor suppressant concentrate can be added to the crude oil at any point in the recovery, extraction, processing, transportation, and/or storage of the crude oil. In some embodiments, the paraffin suppressant concentrate is a paraffin suppressant concentrate. In embodiments, the paraffin inhibitor is present in the paraffin inhibitor concentrate at about 1 wt % to about 5 wt %, in embodiments at about 2 wt % to 3 wt %. In embodiments, the concentrate is diluted the field to about 50 ppm to 10,000 ppm paraffin inhibitor by adding the paraffin inhibitor concentrate to a crude oil, optionally often along with one or more additional additives to accomplish e.g. biocidal activity, corrosion resistance, and the like. Petroleum-based solvents that conventionally provide the balance of paraffin inhibitor concentrate compositions comprise, consist essentially of, or consist of a refined petroleum solvent. Refined petroleum solvents comprise, consist essentially of, or consist of aromatic compounds such as benzene, toluene, xylene, light aromatic naphtha, heavy aromatic naphtha, kerosene, or diesel; and/or aliphatic compounds such as pentane, hexane, heptane, octane, nonane, decane, undecane, dodecane, tridecane, tetradecane, pentadecane, hexadecane, or any of their cyclic or branched isomers or a mixture thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is lower boiling material collected near the top portion of the distillation column; medium naphtha higher boiling material from near the middle. Heavy naphtha is an even higher boiling material from near the bottom portion of the column.

Twenty-Third Embodiments

In twenty-third embodiments, there is provided a method of tracing a paraffin suppressant in crude oil comprising adding a paraffin suppressant composition comprising any one or more of the graphene tagged paraffin inhibitors, graphene tagged paraffin dispersants, and graphene tagged paraffin suppressants herein to a crude oil composition to form a graphene tagged crude oil composition; irradiating the graphene tagged crude oil composition with a source of light having a selected first range of wavelengths; and measuring the luminescent emission of the graphene quantum dot at a selected second range of wavelengths, wherein the measuring is carried out substantially contemporaneously with the irradiating. In embodiments the first range of wavelengths is substantially a single wavelength, herein a "single first wavelength". In embodiments, the single first wavelength of the source of light is about 500 nm. In embodiments, the second range of wavelengths is about 600 nm to 700 nm. In embodiments, the second range of wavelengths is substantially a single wavelength, herein a "single second wavelength". In embodiments, the single second wavelength is about 600 nm.

The fluorescent emission, i.e. luminescence spectra of the graphene tagged paraffin suppressants of the invention fluorescent treatment compounds have a highly advantageous property thereof: the luminescent emission of the suppressants can easily be separated from the fluorescent emissions of hydrocarbons and other compounds and materials entrained in crude oil. For example, Karpicz, R., et al., *Lithuanian* 1 Physics (2005) 45:213-218 report the peak emission wavelengths of crude hydrocarbon oil to be in the range of about 500 nm to 550 nm in many instances, with some refined petroleum products having peak emission intensity somewhat lower than this (e.g. 375 nm-450 nm). Thus the peak emission intensity of the suppressants comprising graphene quantum dots are easily differentiated from the "background" emission of the crude hydrocarbon oil by selecting suppressants whose graphene quantum dots have a peak emission intensity greater than 550 nm, for example 575 nm or greater, such as up to 650 nm, for example. By sufficiently separating the "background" fluorescence of materials present in crude oil and/or compositions comprising crude oil from the fluorescence emission of the graphene quantum dots of the graphene tagged paraffin suppressants, the concentration of the graphene tagged paraffin suppressants in the crude oil is easily measured in the presence of the crude oil and any materials entrained in or added to the crude oil.

Thus, in embodiments, there is provided a method of tracing a paraffin suppressant in crude oil comprising: adding a paraffin suppressant composition or a paraffin suppressant concentrate comprising any one or more of the graphene tagged paraffin inhibitors, graphene tagged paraffin dispersants, or graphene tagged paraffin suppressants described herein to a crude oil composition to form a graphene tagged crude oil composition; irradiating the graphene tagged crude oil composition with a source of light having a selected first range of wavelengths; and measuring the luminescent emission of the graphene quantum dot at a selected second range of wavelengths, wherein the measuring is carried out substantially contemporaneously with the irradiating. In embodiments the first range of wavelengths is substantially a single wavelength, herein a "single first wavelength". In embodiments, the single first wavelength of the source of light is about 500 nm. In embodiments, the second range of wavelengths is about 600 nm to 700 nm. In embodiments, the second range of wavelengths is substantially a single wavelength, herein a "single second wavelength". In embodiments, the single second wavelength is about 600 nm. In embodiments, a graphene tagged paraffin suppressant is added to a first crude oil or composition comprising a crude oil at a first location, the first crude oil or composition comprising crude oil is conveyed by one or more of various means in a crude oil containment to a second location, a sample of a second crude oil or composition containing crude oil is retrieved at the second location, and the luminescent emission at λmax or the luminescent emission spectrum of the sample, a portion of the sample, or a composition comprising the sample or a portion of the sample is measured by fluorometric analysis to determine the concentration of the paraffin suppressant in the sample of the crude oil or composition comprising the crude oil. In embodiments, the first crude oil or composition comprising crude oil is diluted by the addition of other materials such as further crude oil or compositions comprising crude oil, produced water, surfactants, organic solvents, produced water, or other liquids or solids to form the second crude oil or composition comprising crude oil. In embodiments, the second crude oil or composition comprising crude oil comprises, consists of, or consists essentially of the first crude oil or composition comprising the crude oil.

Fluorometric analysis can be conducted using a light source and a fluorescence detector (e.g., fluorometer) configured to fluorometrically detect fluorescence as known in the art. In some embodiments, the fluorometric analysis is carried out using a light source capable of shining light at a particular wavelength, or range thereof, into a graphene tagged crude oil composition.

The invention provides the ability to monitor and control the dosage of paraffin suppressants online and in real time. The ability to automate treatment of crude oils with paraffin suppressants improves the efficiency and reduces total cost of operation of oil recovery and/or oil processing systems. The graphene tagged paraffin suppressants are usefully applied to crude oils that exhibit background (native) fluorescence when exposed to certain excitation wavelengths. In certain embodiments, the invention overcomes issues related to signal interference (i.e., overlap of quantum dot fluorescence and crude oil background fluorescence). In embodiments, crude oils exhibit fluorescence emissions at wavelengths of less than about 550 nm. In some such embodiments, the graphene quantum dots of paraffin suppressants exhibit fluorescence at wavelengths greater than about 550 nm. Thus, in certain embodiments, a graphene quantum dot has a fluorescence emission wavelengths that do not substantially overlap with the fluorescence emissions of the crude oil treated with a paraffin suppressant comprising the graphene quantum dot. In some such embodiments, the graphene quantum dot has a fluorescence emission wavelength that does not overlap with any fluorescence emission wavelengths of the crude oil treated.

In embodiments, the paraffin inhibitor suppressant composition comprises, consists essentially of, or consists of a graphene tagged paraffin suppressant. In embodiments, the graphene tagged paraffin suppressant is a graphene tagged paraffin inhibitor. In embodiments, the graphene tagged paraffin suppressant is a graphene tagged paraffin dispersant. In embodiments, the paraffin suppressant composition further comprises one or more organic solvents. In embodiments, the one or more organic solvents comprises, consists of, or consists essentially of one or more hydrocarbon solvents. In embodiments, the one or more organic solvents comprises, consists of, or consists essentially of one or more hydrocarbon solvents and one or more low boiling solvents. In some embodiments, the paraffin inhibitor suppressant composition is added to crude oil in an oil extraction process, wherein oil is extracted from a subterranean oil reservoir in, for example, an oil field. In some embodiments, the oil extraction process is an enhanced oil recovery process selected from fracking or gas lift oil recovery.

In some embodiments, the paraffin inhibitor suppressant composition is added to crude oil in a subterranean reservoir. In some embodiments, the paraffin inhibitor composition is added to the crude oil after the crude oil emerges from the subterranean reservoir. In some embodiments, the paraffin inhibitor suppressant composition is added to the crude oil below ground. In some embodiments, the paraffin inhibitor suppressant composition is added to the crude oil above ground. In some embodiments, the paraffin inhibitor suppressant composition is added to the crude oil by introducing the composition into the crude oil via a capillary string. In some embodiments, the crude oil is contained within a subterranean reservoir. In some embodiments, the paraffin inhibitor suppressant composition is added to the crude oil via an annulus of a downpipe which is in communication with a subterranean oil reservoir. In some embodiments, the paraffin inhibitor suppressant composition is added to crude oil in an oil processing operation such as oil refining and the like. In some embodiments, the paraffin inhibitor suppressant composition is added to crude oil in an oil transportation process such as transportation of oil by oil pipeline. In some embodiments, the paraffin inhibitor suppressant composition is added to crude oil in an oil storage process. The paraffin inhibitor suppressant composition can be added to the crude oil at any point in the recovery, extraction, processing, transportation, and/or storage of the crude oil. In some embodiments, the paraffin suppressant composition is a paraffin suppressant concentrate.

In some embodiments, polymers that are paraffin inhibitors for crude oil also have additional utility as asphaltene dispersants, pour point depressants, flow improvers, and may provide other crude oil benefits known to one skilled in the art. Therefore, in some embodiments the paraffin inhibitor suppressants provide a benefit to crude oil as not only paraffin inhibitor but also as an asphaltene dispersant, pour point depressant, and flow improver and may also provide other crude oil benefits known to one skilled in the art.

Experimental Section

Example 1

An amino-functionalized Graphene Quantum Dot (amino-GQD) was synthesized according to techniques set forth in B. Neises, W. Steglich, *Angew. Chem. Int. Ed.,* 1978, 17, 522-524. The amino-GQD was then reacted with a polymeric paraffin inhibitor in the following manner. The paraffin inhibiting polymer is similar to the comblike polymer described in Xu, J. et al., *Asia-Pac. J. Chem. Eng.* 2009; 4; 551-556.

First, 130 mg of a C20-C24 α-olefin/maleic anhydride copolymer was mixed into 5 mL ethyl acetate until fully dispersed. Then the mixture was stirred in an ice bath and a C20+ fatty alcohol was added to the mixture in an amount corresponding to 0.97 molar equivalents based on equivalents of maleic anhydride. Then 25 mg amino-GQD was added to the mixture. The mixture was stirred for 10 minutes, then the ice bath was removed and the mixture was stirred for an additional 2 hours.

Finally, ethyl acetate was removed under reduced pressure to yield a solid particulate material. The solid was resuspended by adding 3 mL DI water and 1 drop of acetic acid.

A 40 µL aliquot of the resuspended solid was added to 3 mL DI water, and the diluted resuspended solid was irradiated at a wavelength of 475 nm. The emission maximum was observed at 518 nm.

The invention illustratively disclosed herein can be suitably practiced in the absence of any element which is not specifically disclosed herein. Additionally each and every embodiment of the invention, as described herein, is intended to be used either alone or in combination with any other embodiment described herein as well as modifications, equivalents, and alternatives thereof. In various embodiments, the invention suitably comprises, consists essentially of, or consists of the elements described herein and claimed according to the claims. It will be recognized that various modifications and changes may be made without following the example embodiments and applications illustrated and described herein, and without departing from the scope of the claims.

The invention claimed is:

1. A paraffin inhibiting composition comprising a paraffin inhibiting polymer effective for suppressing the phase separation of paraffin wax from crude oil; and a graphene quantum dot covalently bonded to the paraffin inhibiting polymer, wherein the graphene quantum dot has a particle size of about 2 nm to 20 nm.

2. The paraffin inhibiting composition of claim 1 wherein the paraffin inhibiting polymer comprises the residue of one or more α-olefins, one or more fatty alcohols, or both, wherein each of the one or more α-olefins, the one or more fatty alcohols, or both independently comprises an alkyl group having between 5 and 60 carbons.

3. A graphene tagged crude oil composition comprising:
   crude oil; and
   a paraffin inhibiting composition according to claim 1.

4. The graphene tagged crude oil composition of claim 3 comprising about 5 ppm to 5000 ppm by weight of the paraffin inhibiting composition.

5. The graphene tagged crude oil composition of claim 3 comprising about 0.1 ppb to 1 ppm by weight of the graphene quantum dot.

6. The paraffin inhibiting composition of claim 1 formed by a method comprising:
   combining a graphene quantum dot with a reactive paraffin inhibitor polymer to form a reactive mixture, the graphene quantum dot having a particle size of about 2 nm to 20 nm and comprising a hydroxyl or amino functionality, and the reactive paraffin inhibitor polymer comprising one or more anhydride, carboxylate, carboxylic acid, carboxylic acid ester groups, or a mixture thereof; and
   subjecting the reactive mixture to conditions suitable for causing a reaction of an amino or hydroxyl functionality with an anhydride, carboxylate, carboxylic acid, or carboxylic acid ester group to result a tagged paraffin inhibiting polymer.

7. The composition of claim 6 wherein the reactive paraffin inhibitor polymer comprises maleic anhydride functionality.

8. A paraffin inhibiting composition comprising a graphene quantum dot having a particle size of about 2 nm to 20 nm dispersed in a hydrophobic liquid; and one or more paraffin dispersants.

9. The paraffin inhibiting composition of claim 8, wherein the one or more paraffin dispersants comprises an ammonium salt of a long-chain alkyl benzene sulfonic acid, an alkoxylated long-chain alkyl phenol, an alkoxylated long-chain alcohol, or a mixture thereof.

10. The paraffin inhibiting composition of claim 8 further comprising an α-olefin-maleic anhydride copolymer, an ethylene-vinyl acetate copolymer, a long-chain acrylic polymer, a long-chain-alkyl phenol-formaldehyde resin, an alkoxylated long-chain-alkyl phenol, an alkoxylated long-chain alcohol, an ammonium salt of a long-chain-alkyl benzene sulfonate, or a mixture thereof.

11. A method of measuring the amount of paraffin inhibitor in a crude oil, the method comprising:
adding about 5 ppm to 5000 ppm by weight of a paraffin inhibiting composition to a crude oil to form a graphene tagged crude oil composition, the paraffin inhibiting composition comprising a paraffin inhibiting polymer effective for suppressing the phase separation of paraffin wax from crude oil, and a graphene quantum dot covalently bonded to the paraffin inhibiting polymer, wherein the graphene quantum dot has a particle size of about 2 nm to 20 nm;
irradiating the graphene tagged crude oil composition with a source of light having a selected first range of wavelengths; and
measuring a luminescent emission of the graphene tagged crude oil composition at a selected second range of wavelengths, wherein the measuring is carried out substantially contemporaneously with the irradiating.

12. The method of claim 11 wherein the first range of wavelengths is substantially a single first wavelength.

13. The method of claim 12 wherein the single second wavelength is between about 500 nm to 550 nm.

14. The method of claim 11 wherein the second range of wavelengths is substantially a single second wavelength.

15. The method of claim 14 wherein the single second wavelength is between about 600 nm and 700 nm.

\* \* \* \* \*